(12) United States Patent
Ito

(10) Patent No.: US 10,809,274 B2
(45) Date of Patent: Oct. 20, 2020

(54) METHOD AND DEVICE FOR MOVING OBJECT

(71) Applicant: YAMAHA HATSUDOKI KABUSHIKI KAISHA, Iwata-shi, Shizuoka-ken (JP)

(72) Inventor: Saburo Ito, Shizuoka (JP)

(73) Assignee: YAMAHA HATSUDOKI KABUSHIKI KAISHA, Iwata-shi, Shizuoka-ken (JP)

( * ) Notice: Subject to any disclaimer, the term of this patent is extended or adjusted under 35 U.S.C. 154(b) by 228 days.

(21) Appl. No.: 15/743,607

(22) PCT Filed: Mar. 17, 2016

(86) PCT No.: PCT/JP2016/058491
§ 371 (c)(1),
(2) Date: Jan. 10, 2018

(87) PCT Pub. No.: WO2017/017990
PCT Pub. Date: Feb. 2, 2017

(65) Prior Publication Data
US 2018/0203028 A1 Jul. 19, 2018

(30) Foreign Application Priority Data

Jul. 28, 2015 (JP) .................. 2015-148613

(51) Int. Cl.
*G01N 35/10* (2006.01)
*C12M 1/26* (2006.01)
*G01N 1/14* (2006.01)

(52) U.S. Cl.
CPC ............ *G01N 35/10* (2013.01); *C12M 33/04* (2013.01); *G01N 1/14* (2013.01); *G01N 35/1009* (2013.01);
(Continued)

(58) Field of Classification Search
None
See application file for complete search history.

(56) References Cited

U.S. PATENT DOCUMENTS 5,139,743 A 8/1992 Ishizaka et al.
5,525,302 A * 6/1996 Astle .................. B01L 3/0279
422/511
(Continued)

FOREIGN PATENT DOCUMENTS

CN 102740978 A 10/2012
JP S64-080863 A 3/1989
(Continued)

OTHER PUBLICATIONS

An Office Action mailed by the Japanese Patent Office dated Jul. 23, 2019, which corresponds to Japanese Patent Application No. 2015-148613 and is related to U.S. Appl. No. 15/743,607; with English language translation.
(Continued)

*Primary Examiner* — Jill A Warden
*Assistant Examiner* — Brittany I Fisher
(74) *Attorney, Agent, or Firm* — Studebaker & Brackett PC

(57) ABSTRACT

There are prepared a first container which stores a liquid containing a cellular aggregate, a second container which receives a cellular aggregate, and a third container which stores a preliminary treatment solution, and a cylinder tip. The cylinder tip is formed with a syringe including a tubular passage having a front end opening which sucks the cellular aggregate, and a plunger which reciprocates in a tubular passage. Before sucking the cellular aggregate from the first container and discharging the same to the third container, the preliminary treatment solution is retained in a space between the tubular passage and the plunger by dipping the front end opening of the cylinder tip into the preliminary treatment
(Continued)

solution in the third container and causing the plunger to reciprocate.

6 Claims, 18 Drawing Sheets

(52) U.S. Cl.
CPC . *G01N 35/1074* (2013.01); *G01N 2001/1427* (2013.01)

(56) References Cited

U.S. PATENT DOCUMENTS

| | | | | |
|---|---|---|---|---|
| 8,871,157 | B2* | 10/2014 | Homberg | B01L 3/0237 422/508 |
| 2002/0164272 | A1* | 11/2002 | Harris | B01L 99/00 73/864.44 |
| 2005/0084423 | A1 | 4/2005 | Zarowitz et al. | |
| 2006/0275892 | A1* | 12/2006 | Shibazaki | B01L 3/0275 435/287.2 |
| 2007/0020763 | A1* | 1/2007 | Ingenhoven | G01N 1/14 436/43 |
| 2007/0084302 | A1* | 4/2007 | Tsuchihashi | G01N 30/24 73/864.11 |
| 2010/0101652 | A1* | 4/2010 | Shiraishi | G01N 35/1095 137/1 |
| 2013/0017127 | A1* | 1/2013 | Tokumaru | C12M 23/10 422/509 |
| 2013/0074614 | A1* | 3/2013 | Holmes | B01L 3/50825 73/864.01 |
| 2013/0108521 | A1* | 5/2013 | Ikushima | B05B 15/55 422/509 |
| 2013/0330250 | A1 | 12/2013 | Koeda et al. | |
| 2014/0106467 | A1* | 4/2014 | Hutter | G01N 35/1004 436/180 |
| 2014/0370589 | A1* | 12/2014 | Ito | B01L 3/0275 435/309.1 |
| 2015/0369834 | A1 | 12/2015 | Tokumaru | |
| 2016/0341756 | A1* | 11/2016 | Hirano | G01F 22/02 |
| 2017/0001190 | A1 | 1/2017 | Ito | |

FOREIGN PATENT DOCUMENTS

| | | |
|---|---|---|
| JP | 2009-034013 A | 2/2009 |
| JP | 2013-017461 A | 1/2013 |
| JP | 2013-252078 A | 12/2013 |
| WO | 2005/039772 A2 | 5/2005 |
| WO | 2011/075075 A1 | 6/2011 |
| WO | 2015/079476 A1 | 6/2015 |
| WO | 2015/079477 A1 | 6/2015 |

OTHER PUBLICATIONS

International Search Report issued in PCT/JP2016/058491; dated Jun. 21, 2016.

The extended European search report issued by the European Patent Office dated Jul. 9, 2018, which corresponds to European Patent Application No. 16830095.2 -1001 and is related to U.S. Appl. No. 15/743,607.

* cited by examiner

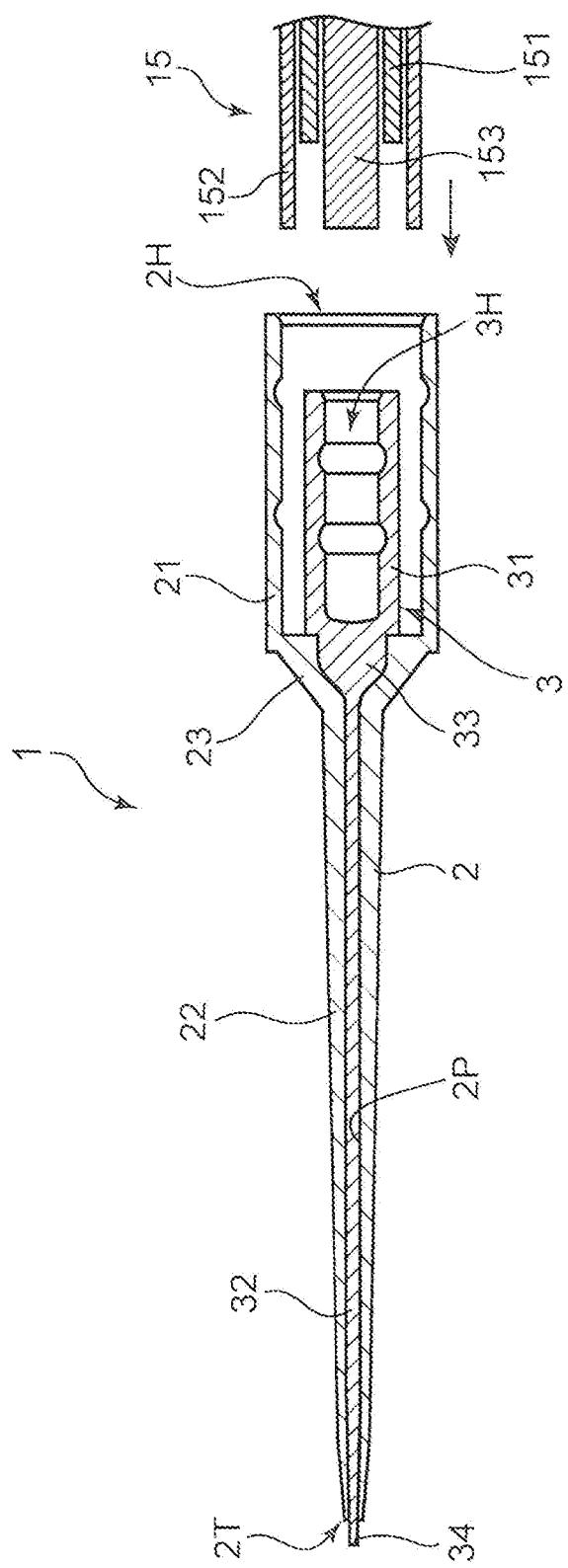

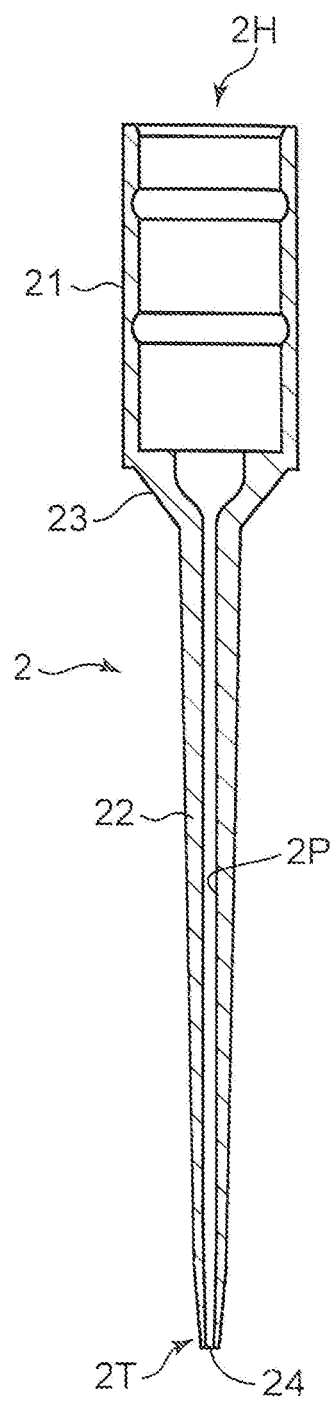
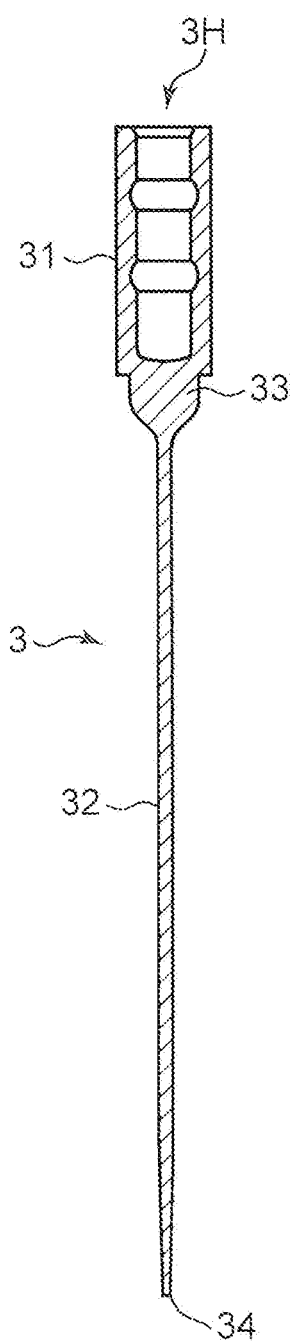
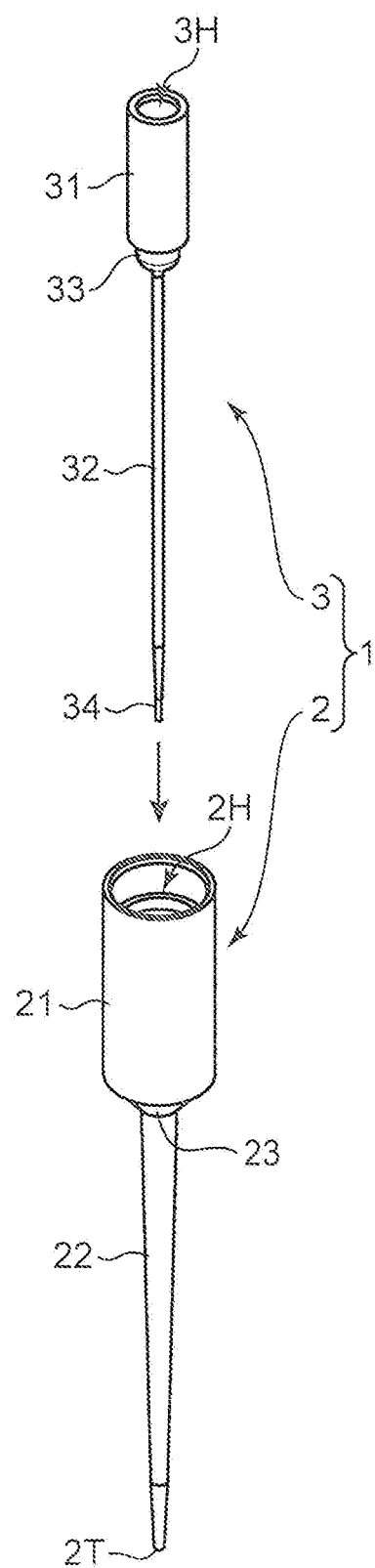

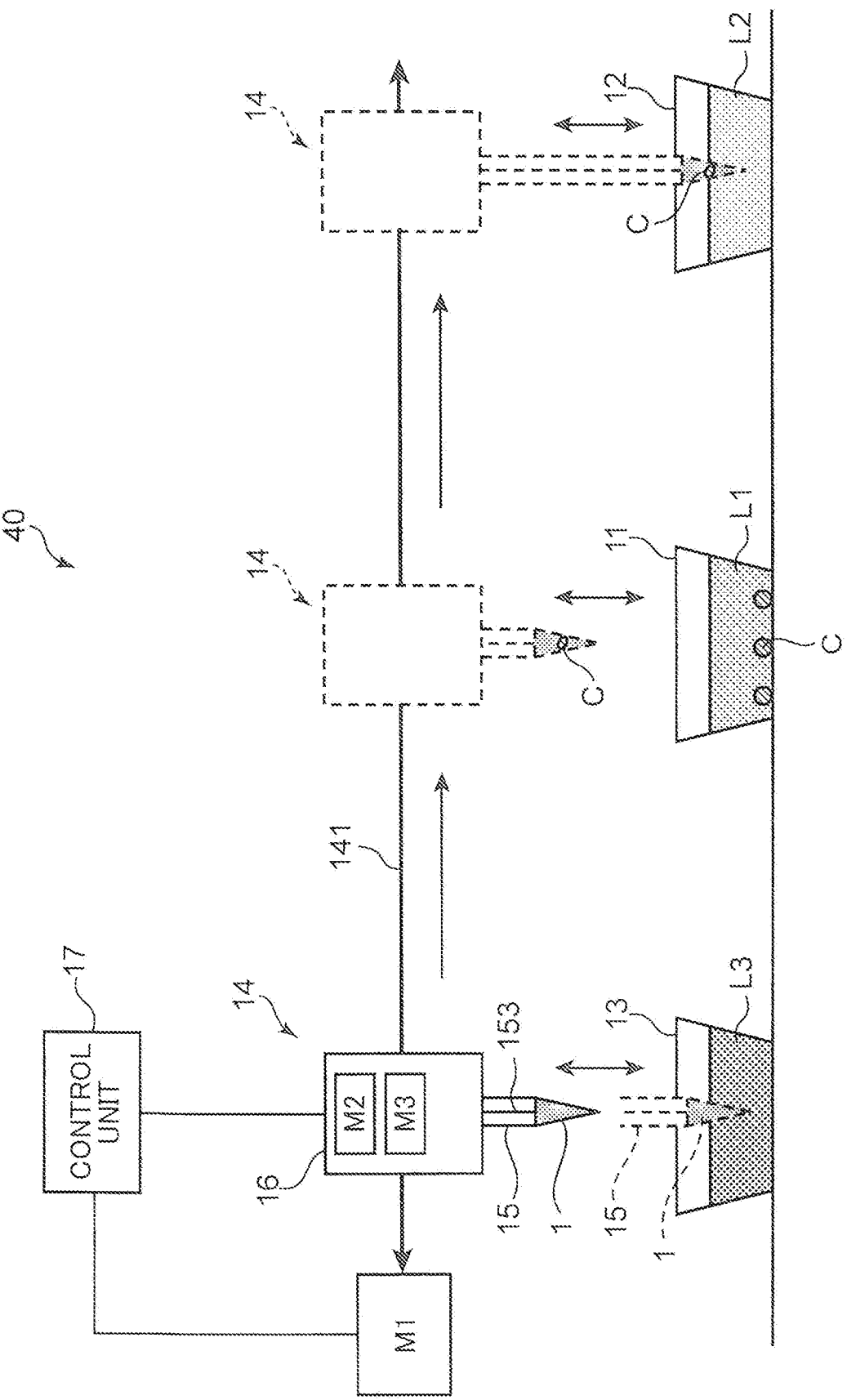

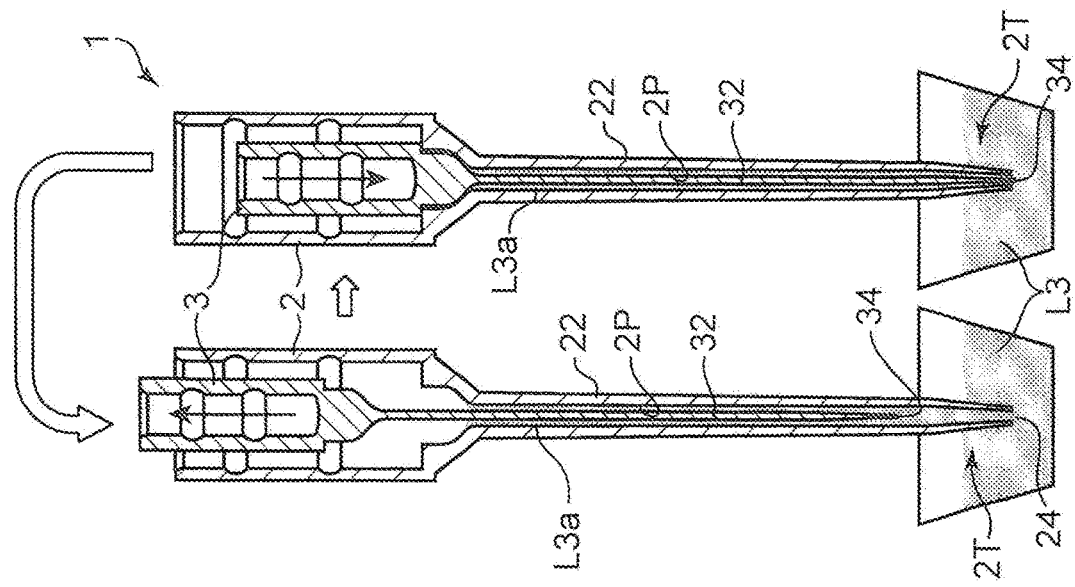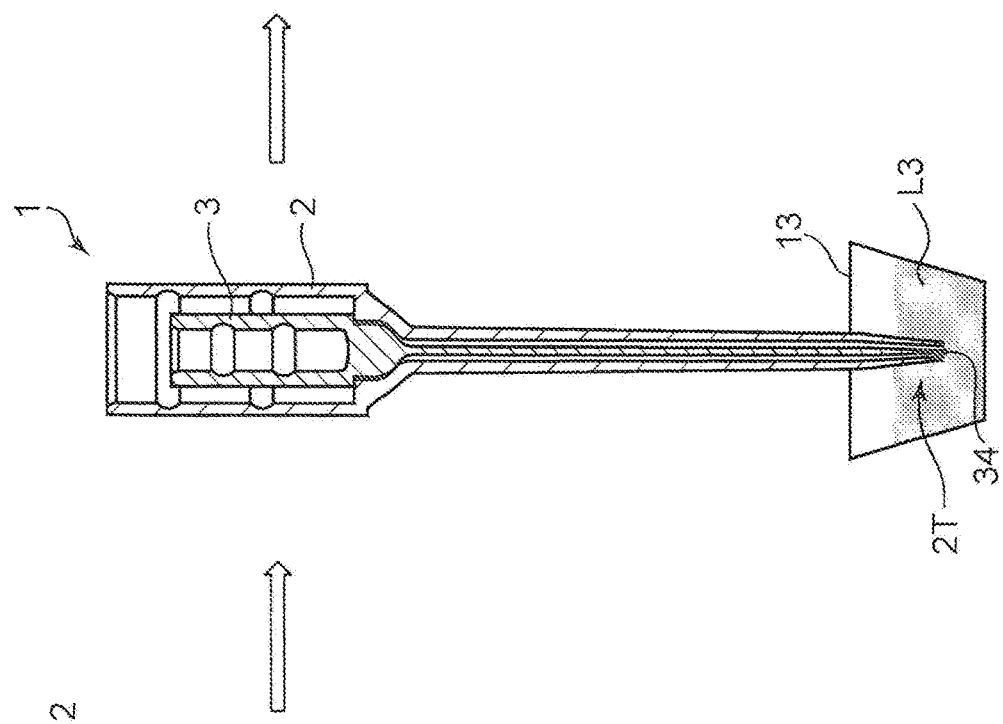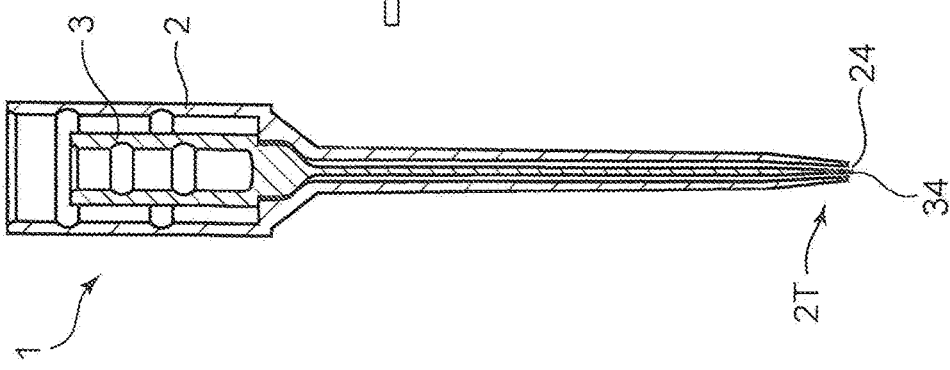

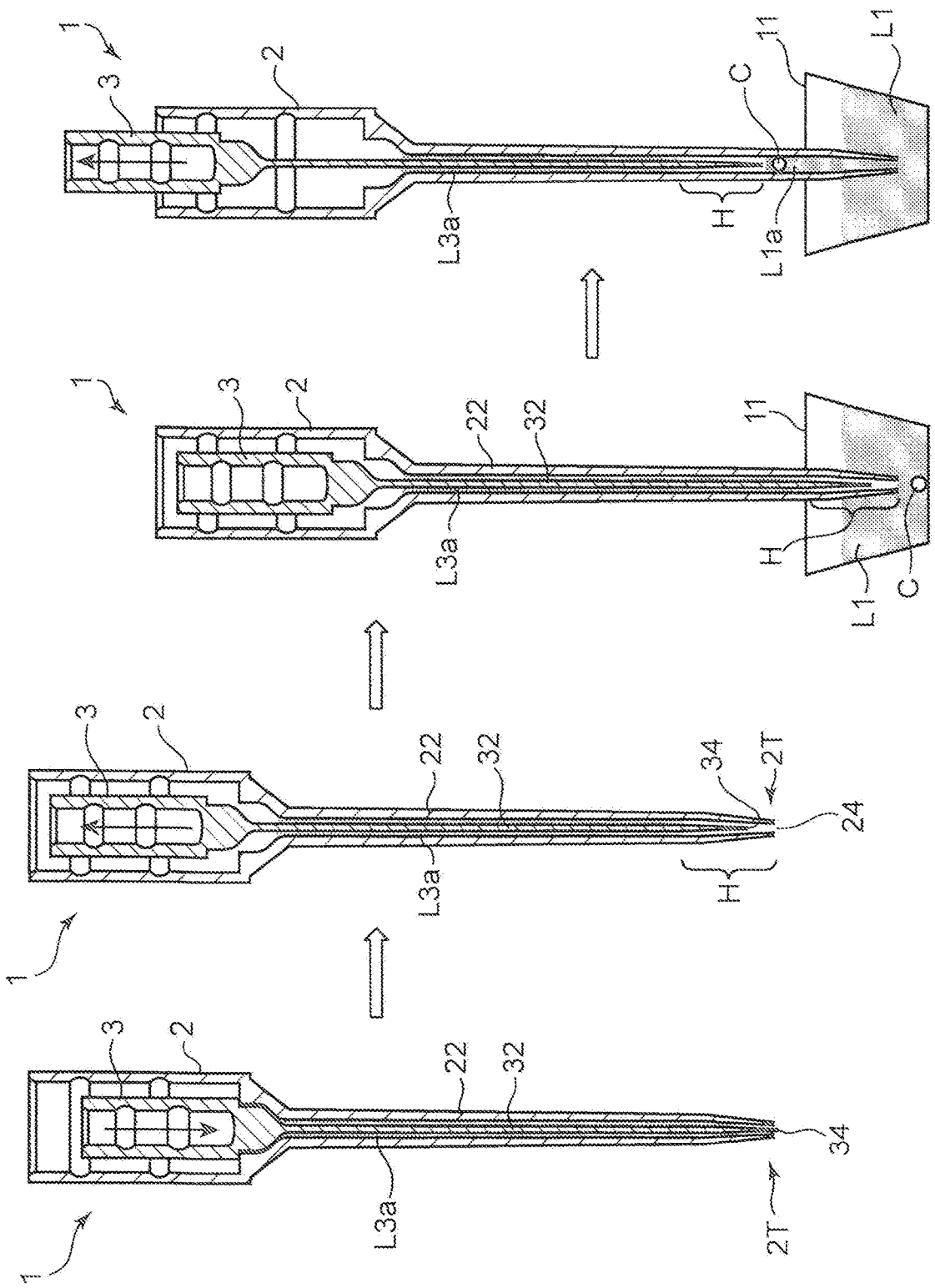

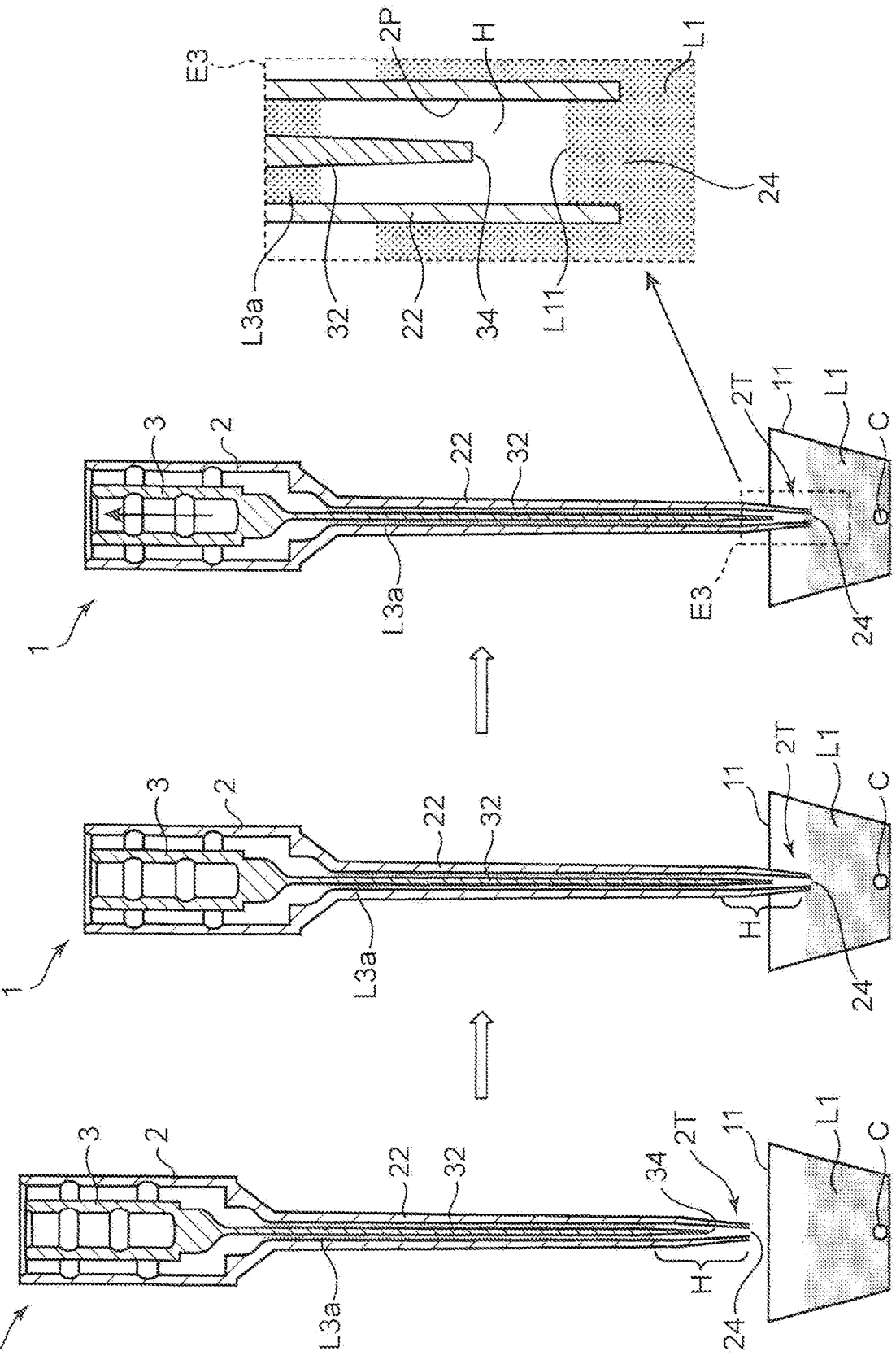

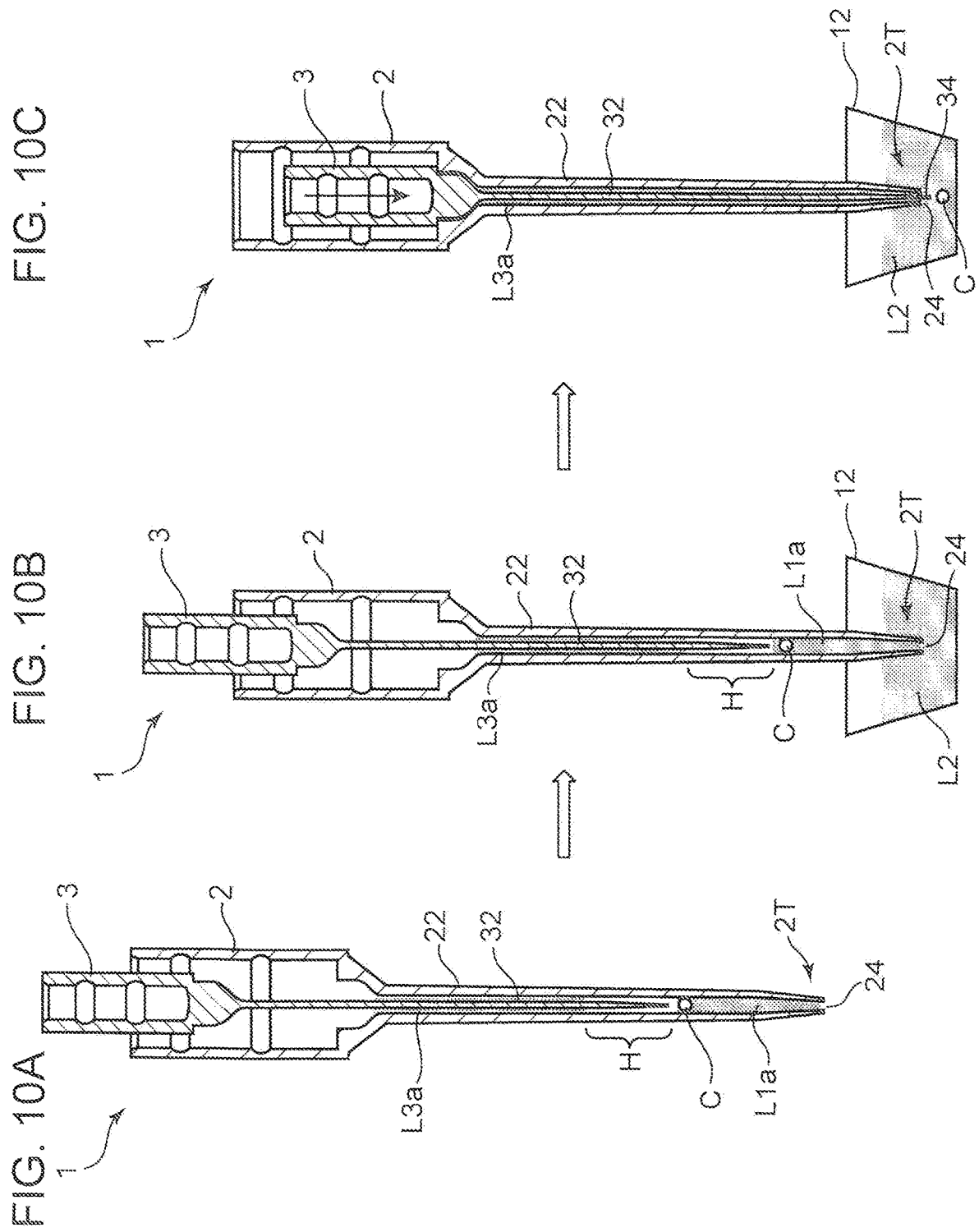

METHOD AND DEVICE FOR MOVING OBJECT

CROSS-REFERENCE TO RELATED APPLICATION

This application is a National Stage of International Patent Application No. PCT/JP2016/058491, filed Mar. 17, 2016, which claims benefit to Japanese Patent Application No. 2015-148613, filed on Jul. 28, 2015, the entire contents of both are incorporated herein by reference.

TECHNICAL FIELD

The present disclosure relates to a method and a device for moving a minute object, such as a cellular aggregate, between containers.

BACKGROUND ART

For moving a minute object, a tip may be used which is formed of a syringe including a tubular passage, and a plunger which reciprocates in the tubular passage. For a purpose of, for example, medical or biological studies, the tip is used at the time of moving a cellular aggregate from a first container which stores the same to a second container (e.g. well plate) in which culture, test, check, observation or the like of the cellular aggregate is conducted. In this case, the tip sucks the cellular aggregate from the first container together with a medium liquid, and discharges the medium liquid containing the sucked cellular aggregate to the second container.

The syringe has a front end opening formed at one end of the tubular passage. Rise of the plunger relative to the syringe to cause generation of a sucking force at the front end opening results in causing the tip to suck an object from the front end opening and temporarily storing the same in the tubular passage. Additionally, fall of the plunger to cause generation of a discharging force at the front end opening results in causing the tip to discharge a stored object from the front end opening (see, for example, Japanese Patent Unexamined Publication No. 2009-34013).

SUMMARY

In such operation of sucking and discharging an object using a tip as described above, there is a case where a sucked object is trapped in the tip, so that the object cannot be discharged in subsequent discharging operation. This is caused by catching of the object between an internal wall surface of a tubular passage of a syringe and a peripheral surface of a plunger.

The present disclosure, which has been made in view of the above point, provides a method and a device for moving an object which enable an object once sucked into a tip to be discharged satisfactorily without being trapped in the tip.

An object moving method according to one aspect of the present disclosure includes a step of preparing a tip including a syringe having a front end opening for sucking an object and a tubular passage with one end leading to the front end opening, and a plunger which reciprocates in the tubular passage; a step of dipping the front end opening of the syringe into a predetermined preliminary treatment solution and causing the plunger to reciprocate, thereby retaining the preliminary treatment solution in a space between the tubular passage and the plunger; a step of dipping the front end opening of the syringe into a liquid containing an object and causing the plunger to rise, thereby sucking the object into the tubular passage together with the liquid; and a step of causing the plunger to fall down to discharge the object outside together with the liquid.

An object moving device according to another aspect of the present disclosure includes a first container which stores a liquid containing an object; a second container which receives the object; a third container which stores a preliminary treatment solution; a tip including a syringe having a front end opening for sucking the object and a tubular passage with one end leading to the front end opening, and a plunger which reciprocates in the tubular passage; a head to which the tip is attached and includes a rod that reciprocates the plunger; a head moving mechanism which causes the head to move among the first container, the second container, and the third container; and a control unit which controls operation of the head and the head moving mechanism, in which the control unit executes first control of causing the head to move to a position of the third container to dip the front end opening of the syringe into a preliminary treatment solution in the third container and cause the plunger to reciprocate, thereby retaining the preliminary treatment solution in a space between the tubular passage and the plunger; second control of causing the head to move to a position of the first container to dip the front end opening of the syringe into the liquid in the first container and cause the plunger to rise, thereby sucking the object into the tubular passage together with the liquid, and third control of causing the head to move to a position of the second container to cause the plunger to fall down, thereby discharging the object to the second container together with the liquid.

An objective, features, and advantages of the present disclosure become more apparent from detailed description in the following and accompanying drawings.

BRIEF DESCRIPTION OF THE DRAWINGS

FIG. 1 is a sectional view of a cylinder tip as one example of a tip for use in an object moving method according to the present disclosure;

FIG. 2A is a sectional view of a syringe as a constituent member of the cylinder tip, FIG. 2B is a sectional view of a plunger, and FIG. 2C is an exploded perspective view of the cylinder tip;

FIG. 6 is a view schematically showing a configuration of an object moving device according to the present disclosure;

FIGS. 7A to 7C are views showing a step of retaining a preliminary treatment solution by the cylinder tip in the object moving method;

FIGS. 8A to 8D are views showing a step of forming an air layer in the cylinder tip and a step of sucking a cellular aggregate;

FIGS. 9A to 9C are views showing a preferable pretreatment step in the sucking step;

FIGS. 10A to 10C are views showing a step of discharging a cellular aggregate from the cylinder tip;

DESCRIPTION OF EMBODIMENTS

Figure 3:
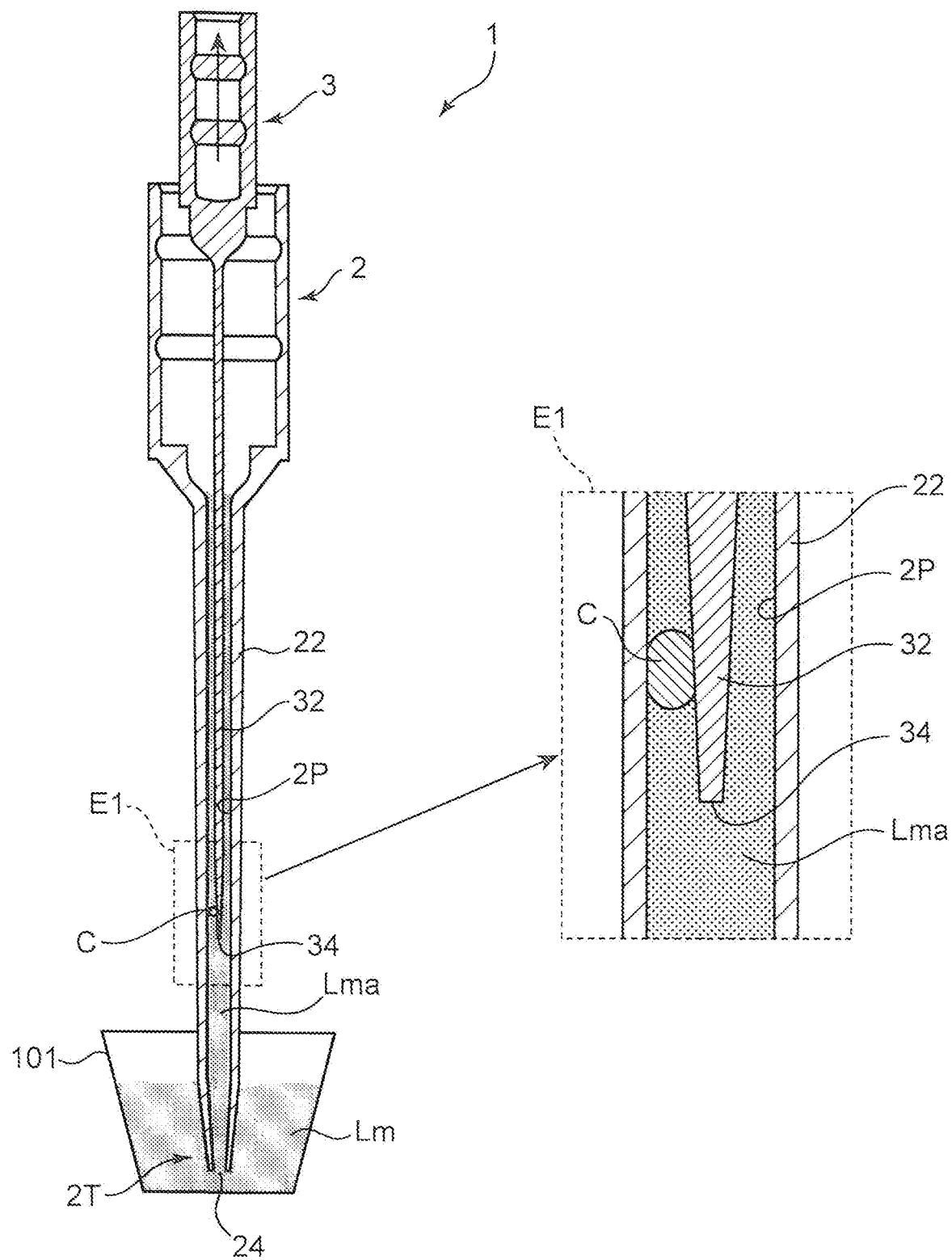
FIG. 3 is a sectional view (a part of which view is expanded) showing Comparative Example of cellular aggregate sucking operation by the cylinder tip.

In the following, an embodiment of the present disclosure will be described in detail with reference to the drawings. FIG. 1 is a sectional view of a cylinder tip as one example of a tip for use in an object moving method according to the present disclosure. A cylinder tip 1 is a member for use in moving a minute object, for example, a cell or a cellular aggregate and is provided with a function of sucking, retaining, and discharging the cellular aggregate together with a medium such as a cell culture solution. The object may be an organic or inorganic minute piece other than a cell. Before description of the object moving method according to the present disclosure, a configuration of the cylinder tip 1 will be described.

The cylinder tip 1 includes a syringe 2 internally provided with a tubular passage 2P (tubular passage) serving as a suction path of a cellular aggregate, and a plunger 3 which reciprocates in the tubular passage 2P while being in contact with an inner wall surface of the syringe 2 defining the tubular passage 2P so as to slide. FIG. 2A is a sectional view of the syringe 2 alone, FIG. 2B is a sectional view of the plunger 3 alone, and FIG. 2C is an exploded perspective view of the cylinder tip 1.

The syringe 2 includes a syringe base end portion 21 formed of a cylindrical body with a large diameter, a syringe main body portion 22 formed of a long cylindrical body with a small diameter, and a tapered cylinder portion 23 linking the base end portion 21 and the main body portion 22. The tubular passage 2P is formed in the syringe main body portion 22. A front end portion 2T formed at one end of the syringe main body portion 22 is provided with a front end opening 24 serving as an object suction port or discharge port. One end of the tubular passage 2P leads to the front end opening 24. The syringe base end portion 21 is continuously connected to the other end side of the syringe main body portion 22 via the tapered cylinder portion 23.

The plunger 3 is a member which is inserted into the tubular passage 2P of the syringe 2 to reciprocate in the tubular passage 2P. The plunger 3 includes a plunger base end portion 31 formed of a cylindrical body, a plunger main body portion 32 having a needle shape, a hemispherical portion 33 linking the base end portion 31 and the main body portion 32, and a plunger front end portion 34 as a projecting front end of the plunger main body portion 32.

The syringe base end portion 21 includes a hollow portion 2H having a cylindrical shape. The plunger base end portion 31 has an outer diameter set to be smaller by a predetermined length than an inner diameter of the hollow portion 2H. The plunger main body portion 32 has an outer diameter set to be slightly smaller than an inner diameter of the tubular passage 2P. Additionally, a shape of an inner circumference surface of the tapered cylinder portion 23 matches a curved shape of an outer circumference surface of the hemispherical portion 33. The plunger 3 is installed in the syringe 2 in such a manner that the plunger base end portion 31 is housed in the hollow portion 2H, and the plunger main body portion 32 is inserted in the tubular passage 2P of the syringe main body portion 22.

While FIG. 2C shows a state where the plunger 3 is pulled out from the syringe 2, FIG. 1 shows a state where the plunger main body portion 32 is inserted deepest into the syringe main body portion 22, that is, a state where the plunger 3 lowers most. At this time, the hemispherical portion 33 is fully received in a cavity of the tapered cylinder portion 23. A length of the plunger main body portion 32 is a little larger than that of the syringe main body portion 22, and in the state in FIG. 1, the plunger front end portion 34 projects from the front end opening 24. Additionally, an inner circumference surface of the syringe base end portion 21 and an outer circumference surface of the plunger base end portion 31 have a gap therebetween.

The plunger 3 is capable of moving upward relative to the syringe 2 in the state shown in FIG. 1. When the plunger 3 moves upward by a predetermined length, the plunger front end portion 34 goes down into the tubular passage 2P. On this occasion, it is possible to cause the front end opening 24 to generate a sucking force, thereby sucking fluid (e.g. a cell culture solution containing a cellular aggregate) around the front end opening 24 into the tubular passage 2P. After the suction, when the plunger 3 is moved downward, the fluid sucked into the tubular passage 2P can be discharged from the front end opening 24.

The cylinder tip 1 is attached to a head 15 whose end portion is shown in FIG. 1. The head 15 includes a first cylindrical rod 151, a second cylindrical rod 152 arranged outside the first cylindrical rod 151, and a plunger rod 153 (rod) arranged in a hollow portion of the first cylindrical rod 151. While the second cylindrical rod 152 is a fixed rod, the plunger rod 153 and the first cylindrical rod 151 independently reciprocate. The plunger base end portion 31 is provided with an attachment hole 3H formed of a cylindrical hollow space. Into the attachment hole 3H, an end portion of the plunger rod 153 is pressed. An upper end surface of the plunger base end portion 31 faces a lower end surface of the first cylindrical rod 151. Into the hollow portion 2H of the syringe base end portion 21, an end portion of the immovable second cylindrical rod 152 is pressed. Up-and-down movement of the plunger rod 153 causes the plunger 3 to move up and down as described above. The first cylindrical rod 151 is lowered when the cylinder tip 1 is detached from the head 15.

As described above, movement of the plunger 3 in an up-down direction relative to the syringe 2 enables an object to be sucked and discharged into/from the cylinder tip 1. However, just simple up-down movement of the plunger 3 might not enable an object once sucked into the cylinder tip 1 to be discharged satisfactorily in some cases. The above case is liable to occur in particular when the cylinder tip 1 is first used. Such a case will be described.

Figure 4:
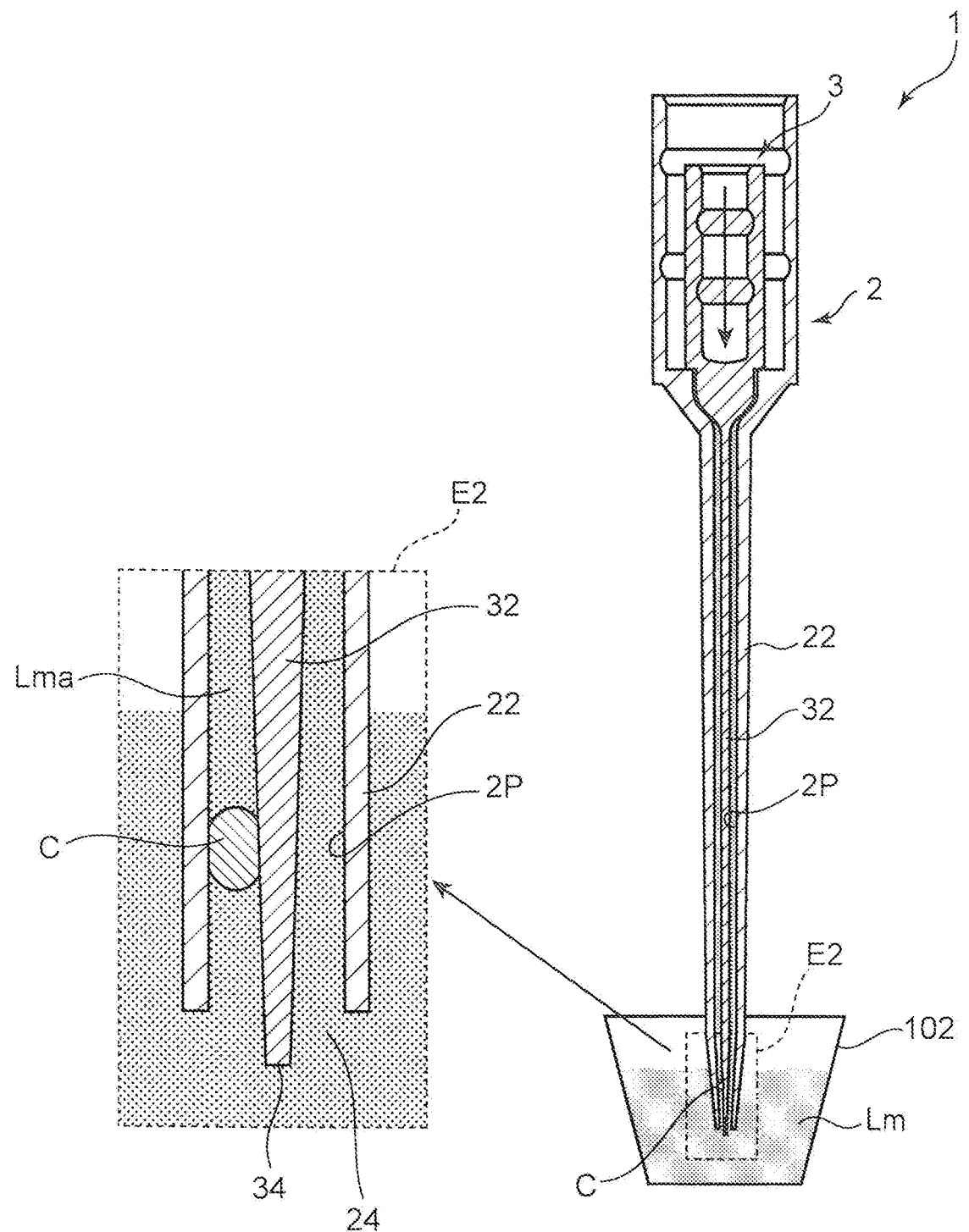
FIG. 4 is a sectional view (a part of which view is expanded) showing Comparative Example of cellular aggregate discharging operation by the cylinder tip.

FIGS. 3 and 4 are sectional views (including expanded parts E1 and E2, respectively) showing Comparative Examples of a cellular aggregate C sucking operation and discharging operation by the cylinder tip 1 in the present embodiment. In FIG. 3, a container 101 is a container which stores a cell culture solution Lm containing the cellular aggregate C. FIG. 3 shows a state where after the front end portion 2T of the syringe 2 is dipped into the cell culture solution Lm in the container 101, the plunger 3 is raised.

When first used, the cylinder tip 1 is in a dry state because no liquid is present in the tubular passage 2P of the syringe main body portion 22. In other words, the tip is in a state where between a wall surface of the tubular passage 2P and a peripheral surface of the plunger main body portion 32, space (an air layer) is present. In this state, when the sucking operation shown in FIG. 3 is executed, there occurs a phenomenon that a sucked cell culture solution Lma sharply rises in the tubular passage 2P due to capillarity in the space or an internal pressure of the tubular passage 2P. The sharp rise of the cell culture solution Lma is followed by a sharp rise of the cellular aggregate C. As a result, the cellular aggregate C might be caught between the syringe main body portion 22 and the plunger main body portion 32 in some cases.

Specifically, more than a necessary amount of the cell culture solution Lma flows into the cylinder tip 1 because of presence of the space, and the cellular aggregate C shifts up to an unintended upper region of the tubular passage 2P, resulting in that the cellular aggregate C is caught in a narrow gap between the syringe main body portion 22 and the plunger main body portion 32 and trapped. A cellular aggregate C of a small size might enter the gap due to a liquid flow of the cell culture solution Lma in the tubular passage 2P even when the space is filled with a liquid.

FIG. 4 shows a state where in the state of FIG. 3, the plunger 3 is lowered in order to discharge the cell culture solution Lma containing the cellular aggregate C. A container 102 is a container which receives the cellular aggregate C and in which the cell culture solution Lm is stored in advance. The plunger 3 is lowered until the plunger front end portion 34 slightly projects from the front end opening 24. At the lowering, the cell culture solution Lma sucked in the cylinder tip 1 is discharged to the container 102. However, the cellular aggregate C might be constrained between the syringe main body portion 22 and the plunger main body portion 32 and not be discharged in some cases. Accordingly, the cellular aggregate C cannot be moved from the container 101 to the other container 102 using the cylinder tip 1 in an intended manner in some cases.

Figure 5:
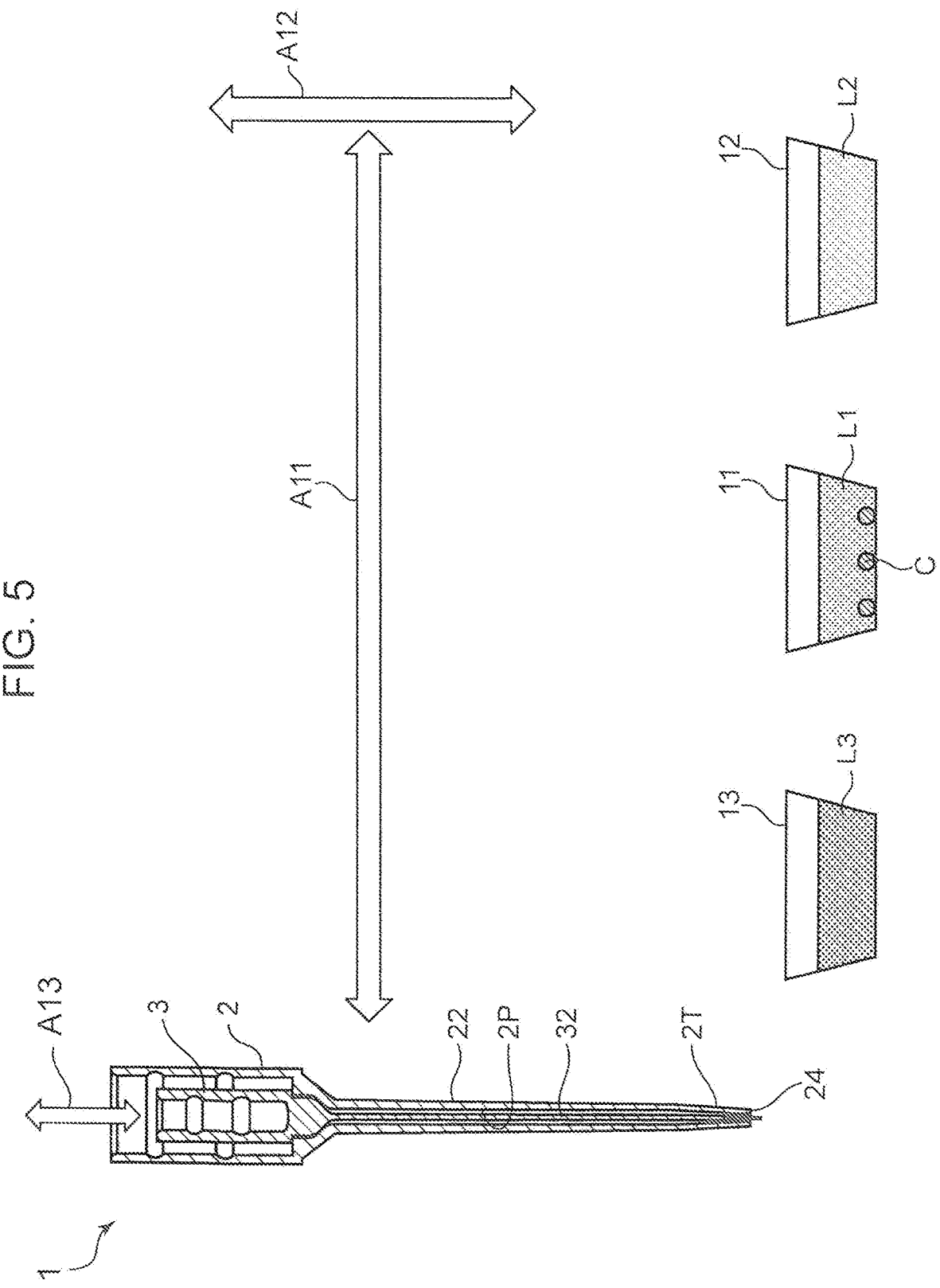
FIG. 5 is a view schematically showing layout of members used in execution of the object moving method according to the present disclosure.

The present embodiment provides a moving method in which the cellular aggregate C is not trapped in the cylinder tip 1. FIG. 5 is a view schematically showing layout of members used in execution of a cell moving method using the cylinder tip 1, which is one embodiment of the object moving method according to the present disclosure. In the present embodiment, there are prepared the cylinder tip 1, and three containers of a first container 11, a second container 12, and a third container 13.

The first container 11 stores a liquid L1 containing the cellular aggregate C as an object. The second container 12, which is a destination of movement of the cellular aggregate C, stores a liquid L2 and receives the cellular aggregate C of the first container 11. The third container 13 stores a preliminary treatment solution L3. The cylinder tip 1 is arranged to be movable above the first, second, and third containers 11, 12, 13 in a horizontal direction as indicated by an arrow A11 and movable in the up-down direction as indicated by an arrow A12 in the figure. Additionally, the plunger 3 moves in the up-down direction relative to the syringe 2 as indicated by an arrow A13.

The cell moving method of the present embodiment includes the following steps (1) to (3) in addition to the above step of preparing the cylinder tip 1 and the above step of preparing the first to third containers 11 to 13.

(1) A preliminary treatment solution retaining step; a step of arranging the cylinder tip 1 to a position of the third container 13 to dip the front end portion 2T (the front end opening 24) of the syringe 2 into the preliminary treatment solution L3, as well as causing the plunger 3 to reciprocate, thereby retaining the preliminary treatment solution L3 in a space between the syringe main body portion 22 and the plunger main body portion 32.

(2) A cell sucking step; a step of moving the cylinder tip 1 to a position of the first container 11 to dip the front end opening 24 of the syringe 2 into the liquid L1, as well as causing the plunger 3 to rise, thereby sucking the cellular aggregate C into the tubular passage 2P together with the liquid L1.

(3) A cell discharging step; a step of moving the cylinder tip 1 to a position of the second container 12 to cause the plunger 3 to fall down, thereby discharging the cellular aggregate C to the second container 12 (outside) together with the liquid L1.

Here, the liquids L1 to L3 will be described. The liquid L1 is not particular limited as long as the liquid does not deteriorate properties of the cellular aggregate C, and can be appropriately selected depending on a kind of the cellular aggregate C. Examples usable as the liquid L1 include a basic medium, a synthetic medium, an Eagle's medium, an RPMI medium, a Fischer's medium, a Ham's medium, an MCDB medium, a BME medium, a BGJB medium, a CMRL 1066 medium, a Glasgow MEM medium, an Improved MEM Zinc Option medium, an IMDM medium, a Medium 199 medium, an Eagle MEM medium, an αMEM medium, a DMEM medium (these media can be combined), and a medium (a cell culture solution) such as blood serum. Other than those, when cultivated without blood serum, examples as a substitute for blood serum include a liquid appropriately containing albumin, amino acid, transferrin, fatty acid, insulin, or the like, a cell freezing solution such as glycerol to be added before refrigerated storage, CELL-BANKER (product of Juji Field Inc.) and the like, formalin, a reagent for fluorescence dyeing, antibody, refined water, physiological saline solution, and the like. When, for example, BxPC-3 (human pancreatic adenocarcinoma cell) which is a cell derived from a living body is used as a cellular aggregate, usable as the liquid L1 is an RPMI-1640 medium mixed with 10% of FBS (Fetal Bovine Serum), with such a supplement as antibiotics, sodium pyruvate, or the like added as required. Also, as the liquid L2 stored in the second container 12, the above liquid can be used.

The preliminary treatment solution L3 stored in the third container 13 is a liquid for in advance filling the space between the syringe main body portion 22 and the plunger main body portion 32 before start of use of the cylinder tip 1. Although a liquid used as the preliminary treatment solution L3 is not particularly limited and may be, for example, physiological saline solution, the above medium is preferably used therefor. In particular, the preliminary treatment solution L3 is preferably substantially equal in component as that of the liquid L1 or the liquid L2.

When the same liquid is used, the first container 11 or the second container 12 may also have the function of the third container 13. When the first container 11 is configured to also have the function of the third container 13, the step of retaining the preliminary treatment solution L3 may be realized by dipping the front end opening 24 of the syringe 2 in the liquid L1 in the first container 11 at a position, for example, where suction of the cellular aggregate C is impossible, and sucking the liquid. This is also the case with the second container 12 configured to also have the function of the third container 13.

In the above cell moving method, since in the preliminary treatment solution retaining step, the preliminary treatment solution L3 is sucked into the cylinder tip 1 in advance, the wall surface of the tubular passage 2P is allowed to enter a state of being wetted with the preliminary treatment solution L3. However, in a case where the liquids L1 and L2 are media (cell culture solutions) of the cellular aggregate C, making these media and the preliminary treatment solution L3 be substantially equal in component to each other prevents change of the components of the liquids L1 and L2 even when these liquids are mixed in the subsequent cell sucking step and cell discharging step.

FIG. 6 is a view schematically showing a configuration of a cell moving device 40 which is one embodiment of an object moving device according to the present disclosure. The cell moving device 40 includes, in addition to the above cylinder tip 1 and first to third containers 11 to 13, a head unit 14, a ball screw 141, a first motor M1, a second motor M2, a third motor M3, and a control unit 17. The head unit 14 includes the head 15 shown in FIG. 1, and a unit main body 16 which is internally provided with the second motor M2 and the third motor M3 and in which the head 15 is installed. The head 15 is a head to which the cylinder tip 1 is attached and which is internally provided with the plunger rod 153 that causes the plunger 3 to reciprocate.

The first motor M1 (a head moving mechanism) is a motor which generates a driving force for causing the ball screw 141 to normally/reversely rotate around an axis. With the ball screw 141, a nut member not shown is engaged. The nut member moves in a right and left direction as a result of driving of the ball screw 141 to rotate. The head unit 14 is attached to the nut member. In other words, the head unit 14 mounted with the cylinder tip 1 is moved in the right and left direction by the driving of the first motor M1. Here, the head unit 14 is movable above the first to third containers 11 to 13.

The second motor M2 is a motor which generates a driving force for causing the head 15 to fall or rise with respect to the unit main body 16. Driving of the second motor M2 enables the head 15 to fall down such that a front end portion of the cylinder tip 1 is dipped into the liquids L1 to L3 in the first to third containers 11 to 13, or enables the head 15 to rise after the dipping.

The third motor M3 is a motor which generates a driving force for causing the plunger rod 153 to reciprocate in the up-down direction. When driving of the third motor M3 causes the plunger rod 153 to be pulled up so that the plunger rises, a sucking force is generated at the front end opening 24 to enable the liquids L1 to L3 to be sucked/retained. By contrast, when the plunger 3 is lowered by pulling down the plunger rod 153, a discharging force is generated at the front end opening 24, so that the liquid retained in the cylinder tip 1 is discharged.

The control unit 17 controls operation of the cell moving device 40 by controlling drive of the first to third motors M1 to M3. Specifically, by controlling drive of the first motor M1, the control unit 17 controls moving operation of the head unit 14 on the ball screw 141, that is, positioning operation of the head 15 in the right and left direction. Additionally, the control unit 17 controls operation of lowering or raising the head 15 by controlling drive of the second motor M2. Further, by controlling drive of the third motor M3, the control unit 17 controls reciprocating operation of the plunger 3, that is, liquid sucking and discharging operation conducted by the cylinder tip 1. In particular, in the present embodiment, the control unit 17 conducts first control of executing the above preliminary treatment solution retaining step, second control of executing the cell sucking step, and third control of executing the cell discharging step. Each step (control) will be described in detail in the following.

FIGS. 7A to 7C are views showing the preliminary treatment solution retaining step (the first control) in the above (1). At the time of execution of the step, a cylinder tip 1 yet to be used is attached to the head 15. The cylinder tip 1 is assumed to be in an initial state as shown in FIG. 7A. Specifically, the cylinder tip 1 is brought to a state where the plunger 3 is lowered most with respect to the syringe 2 and the plunger front end portion 34 slightly projects from the front end opening 24 of the syringe 2. Thereafter, the control unit 17 drives the first motor M1 to move the head unit 14 such that the cylinder tip 1 is located above the third container 13. Then, the control unit 17 drives the second motor M2 to cause the head 15 to fall down until the front end portion 2T of the syringe 2 is sufficiently dipped into the preliminary treatment solution L3 in the third container 13. FIG. 7B shows a state after the fall.

Thereafter, as shown in FIG. 7C, the control unit 17 drives the third motor M3 to execute operation of causing the plunger 3 (the plunger rod 153) to rise and fall down (reciprocating operation) in a predetermined number of cycles. Specifically, by causing the plunger 3 to rise by a predetermined distance until the plunger front end portion 34 is sunk in the syringe 2, the preliminary treatment solution L3 is sucked into the tubular passage 2P from the front end opening 24. Subsequently, by lowering the plunger 3 until the plunger front end portion 34 projects from the front end opening 24, a part of a preliminary treatment solution L3a sucked into the tubular passage 2P is discharged to the third container 13.

Execution of such a sucking and discharging cycle as described above predetermined number of times (e.g. on the order of one to five cycles) results in retaining the sucked preliminary treatment solution L3a in the space between the syringe main body portion 22 and the plunger main body portion 32. In other words, the space is filled in advance with the preliminary treatment solution L3a, so that the cellular aggregate C to be introduced into the cylinder tip 1 in the subsequent cell sucking step cannot easily enter the space.

FIGS. 8A to 8D are views showing the cell sucking step in the above (2). In particular, FIGS. 8A and 8B show a step (fourth control) of forming an air layer in the tubular passage 2P, and FIGS. 8C and 8D show the step (the second control) of sucking the cellular aggregate C, respectively. The control unit 17 drives the second motor M2 in the state shown in FIG. 7C to cause the head 15 to rise, thereby arranging the front end opening 24 of the syringe 2 in the air as shown in FIG. 8A.

Subsequently, the control unit 17 drives the third motor M3 to cause the plunger 3 to rise by a predetermined length as shown in FIG. 8B. As a result, in the tubular passage 2P near the front end opening 24, an air layer H is formed. Specifically, in a sucking direction of the cylinder tip 1, the preliminary treatment solution L3a is present on an upstream side of the tubular passage 2P and the air layer H is present at the most downstream side. In this state, the plunger front end portion 34 is located in the air layer H.

Subsequently, the control unit 17 drives the first motor M1 to move the head unit 14 such that the cylinder tip 1 is located above the first container 11. On this occasion, the cylinder tip 1 is positioned such that the front end opening 24 is located vertically above the cellular aggregate C housed in the first container 11. Applicable for this positioning is a technique, for example, of imaging the first container 11, specifying a position at which the cellular aggregate C is present on the image, and receiving the position as coordinate information by the control unit 17. Then, the control unit 17 drives the second motor M2 to cause the head 15 to fall down until the front end portion 2T of the syringe 2 is dipped into the liquid L1 in the first container 11, to be specific, until the front end opening 24 is located immediately above the cellular aggregate C in the liquid L1. FIG. 8C shows a state after the fall.

Thereafter, the control unit 17 drives the third motor M3 to raise the plunger 3 by a predetermined distance as shown in FIG. 8D. As a result, a part of the liquid L1 in the first container 11 and the cellular aggregate C are sucked from the front end opening 24 into the tubular passage 2P. In the tubular passage 2P, the cellular aggregate C floats in a sucked liquid L1a.

In this cell sucking step, since the preliminary treatment solution L3a is retained in advance in the space between the syringe main body portion 22 and the plunger main body portion 32, the liquid L1 does not sharply rise in the tubular passage 2P due to the above-described capillarity or internal pressure, or the like. Additionally, the air layer H functions as a seal layer which separates, in the tubular passage 2P, the preliminary treatment solution L3a retained in advance in the cylinder tip 1 and the liquid L1a containing the cellular aggregate C sucked thereafter. Accordingly, the sucked cellular aggregate C does not move into the preliminary treatment solution L3a. This prevents the cellular aggregate C from being caught between the syringe main body portion 22 and the plunger main body portion 32. Further, presence of the air layer H prevents the preliminary treatment solution L3a from being mixed with the liquid L1, or prevents the preliminary treatment solution L3a from being discharged to the second container 12 at the subsequent cell discharging step.

FIGS. 9A to 9C are views showing a preferable pretreatment step in the cell sucking step. The pretreatment step is a step of allowing a small amount of the liquid L1 to be retained near the front end opening 24 by dipping the front end opening 24 of the syringe 2 into the liquid L1 in the first container 11 and then raising the plunger 3 by a slight distance. The state of the cylinder tip 1 shown in FIG. 9A is a state where the air layer H is formed at a front end of the tubular passage 2P, which the state corresponds to that of the above FIG. 8B. The cylinder tip 1 is arranged above the first container 11 and the front end opening 24 is positioned at the cellular aggregate C.

Thereafter, the control unit 17 drives the second motor M2 to lower the head 15 until the front end portion 2T of the syringe 2 is dipped into a vicinity of a surface of the liquid L1 in the first container 11 as shown in FIG. 9B. Then, as shown in FIG. 9C, the control unit 17 drives the third motor M3 to raise the plunger 3 by a slight distance. As a result, as shown in an expanded view of a part E3 in the figure, the air layer H moves a little to an upstream side in the sucking direction, while a small amount of the liquid L1 is sucked into the tubular passage 2P near the front end opening 24. A sign L11 in the figure represents the sucked liquid L1.

When the front end portion 2T of the syringe 2 is put into the liquid L1, air might be accumulated near the front end opening 24 partly because a front end of the tubular passage 2P is occupied by the air layer H. When the front end opening 24 is drawn near to the cellular aggregate C to execute the sucking operation, with accumulated air remaining, there might occur a case where appropriate sucking is hindered by pushing of the cellular aggregate C by the accumulated air or the like. However, as shown in FIG. 9C, even when air is accumulated near the front end opening 24, preceded execution of the raising operation of the plunger 3 by a slight distance enables elimination of the accumulated air.

Thereafter, the control unit 17 first drives the second motor M2 to draw the front end opening 24 near to the cellular aggregate C and then, drives the third motor M3 to raise the plunger 3 by a predetermined distance, thereby sucking the cellular aggregate C from the front end opening 24 into the tubular passage 2P. In other words, operation shown in the above FIGS. 8C and 8D are caused to be executed. In this case, since a small amount of a liquid L11 is in advance retained in the tubular passage 2P near the front end opening 24, that is, the front end opening 24 is blocked by the liquid L11, the cellular aggregate C can be smoothly sucked.

FIGS. 10A to 10C are views showing the cell discharging step (the third control) in the above (3). The control unit 17 drives the second motor M2 to cause the head 15 to rise in the state shown in FIG. 8D, thereby causing the cylinder tip 1 retaining the cellular aggregate C to rise as shown in FIG. 10A. Subsequently, the control unit 17 drives the first motor M1 to cause the head unit 14 to move such that the cylinder tip 1 is located above the second container 12. Then, the control unit 17 drives the second motor M2 to cause the head 15 to fall down until the front end portion 2T of the syringe 2 is dipped into the liquid L2 in the second container 12. FIG. 10B shows a state after the fall.

Subsequently, the control unit 17 drives the third motor M3 to cause the plunger 3 to fall down by a predetermined length. To be specific, the plunger 3 is lowered until the plunger front end portion 34 projects from the front end opening 24. As a result, the liquid L1a and the cellular aggregate C retained in the cylinder tip 1 are discharged into the liquid L2 in the second container 12 as shown in FIG. 10C. The foregoing operation completes moving of the cellular aggregate C from the first container 11 to the second container 12. In the discharging operation, the plunger front end portion 34 may not be projected from the front end opening 24 but the plunger front end portion 34 may be lowered to such an extent that allows the air layer H to remain in the syringe 2 (an extent shown in FIG. 9B). In a case, for example, where the liquid L2 is a highly viscous liquid, when the plunger front end portion 34 is fully lowered to cause even the air layer H to be discharged, air bubbles might be left in the liquid L2. In such a case, it is desirable to adjust the degree of fall of the plunger front end portion 34 as described above.

The foregoing present embodiment includes, prior to sucking and discharging of the cellular aggregate C (object) by the cylinder tip 1, the step of retaining a preliminary treatment solution L3a in a space between a wall surface of the tubular passage 2P of the syringe 2 and a peripheral surface of the plunger 3. This allows the space to be filled with the preliminary treatment solution L3a in advance, thereby preventing the cellular aggregate C introduced into the cylinder tip 1 from being caught between the syringe 2 and the plunger 3 in the subsequent cell sucking step. Accordingly, there never occurs a problem that the cellular aggregate C is trapped in the cylinder tip 1 and is not discharged, so that the cellular aggregate C is allowed to have excellent discharging property.

Figure 11:
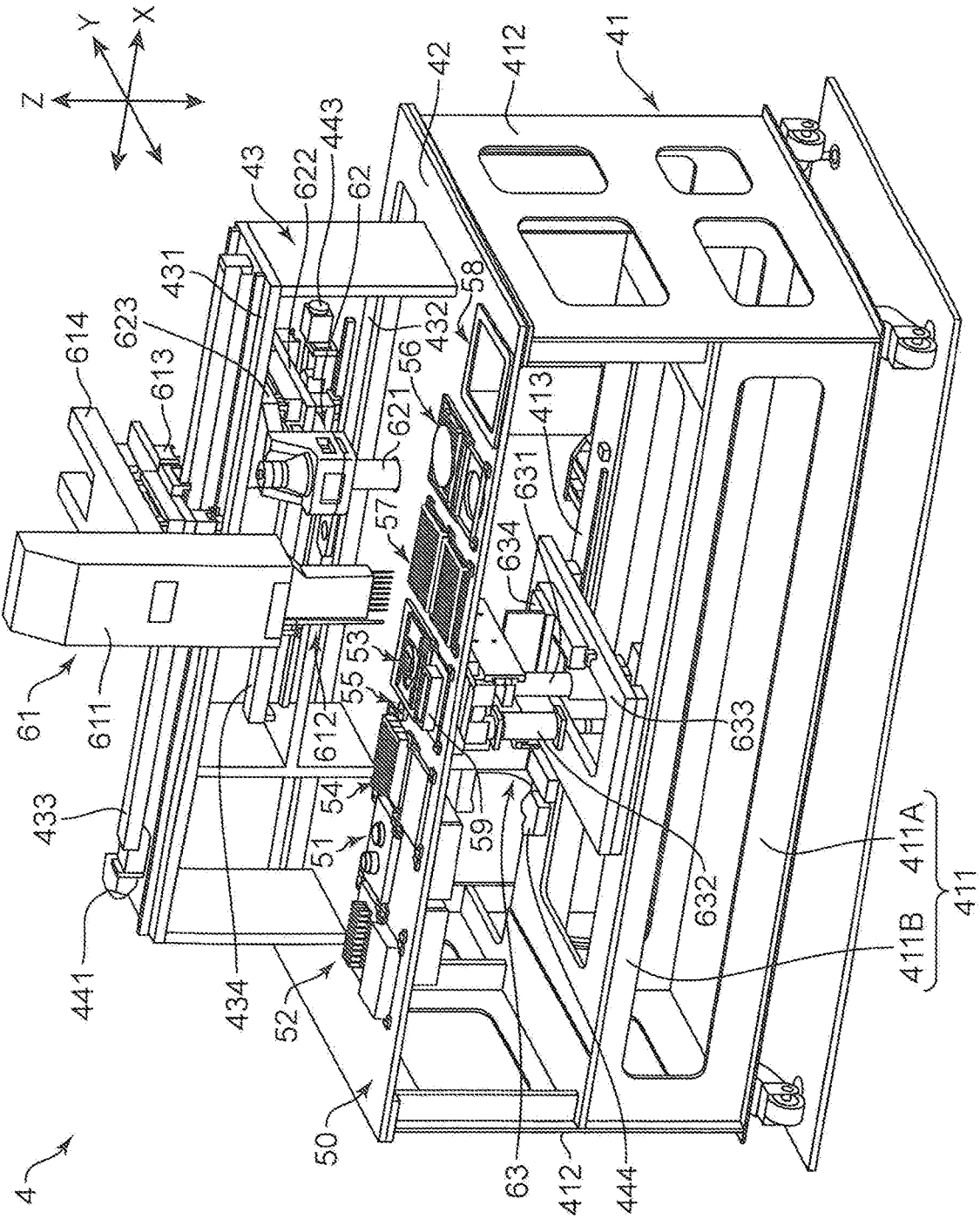
FIG. 11 is a perspective view of a cell moving device as one embodiment of the object moving device according to the present disclosure.
Figure 12:
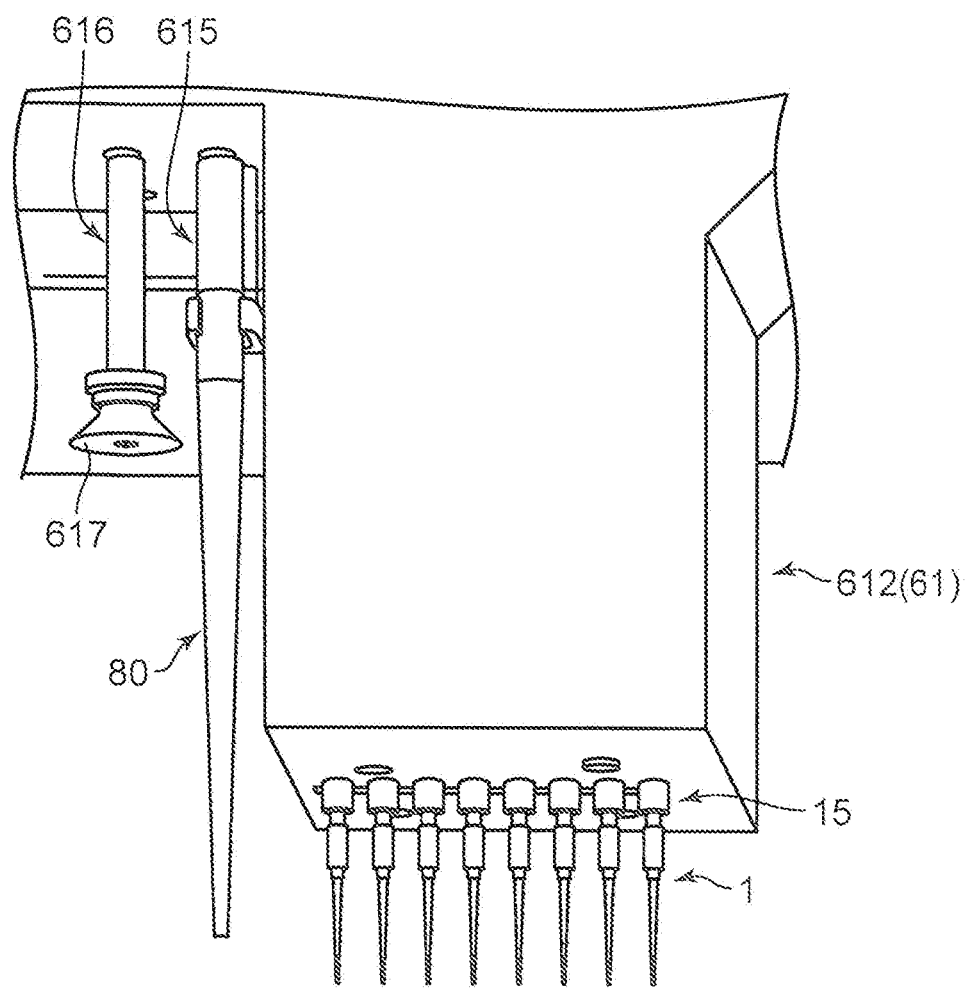
FIG. 12 is a perspective view of a head unit.

Subsequently, a more concrete embodiment of the above cell moving device 40 will be described. FIG. 11 is a perspective view of a multiple-head cell moving device 4 provided with a plurality of the above heads 15. FIG. 12 is a perspective view of a head unit 61 into which a plurality of heads 15 is installed. The cell moving device 4 includes a supporting frame 41, a base 42 supported by the supporting frame 41, a cell moving line 50 installed into the base 42, the head unit 61 and an illumination unit 62 arranged above the base 42, and an imaging unit 63 arranged below the base 42.

The supporting frame 41 includes a base frame 411 and a pair of side frames 412. The base frame 411 is a frame assembly having a rectangular solid shape long in an X direction, which includes a lower layer frame 411A having a rectangular shape, and an upper layer frame 411B provided thereon. On an upper surface of the upper layer frame 411B, a guide rail 413 is provided for moving the imaging unit 63 in the X direction. The base 42 is a rectangular flat plate having a predetermined rigidity, a part or the entire of which is formed of a translucent material, and having substantially the same size as that of the base frame 411 when viewed from above.

On the base 42, a frame stand 43 is vertically arranged. The frame stand 43 includes an upper frame 431 and a middle frame 432 which are flat plates extending in the X direction. On an upper surface of the upper frame 431, an upper guide rail 433 is installed for moving the head unit 61 in the X direction. Additionally, on an upper surface of the middle frame 432, a middle guide rail 434 is installed for moving the illumination unit 62 in the X direction.

The cell moving line 50 is formed with elements arranged in the X direction, the elements being necessary for execution of a series of cell moving steps in which a desired cellular aggregate is extracted from a cell-containing solution and moved to a predetermined container. The cell moving line 50 includes an object stocking portion 51 which stores a cell-containing solution, a dispensation tip stocking portion 52, a cell selection portion 53 for selecting a cellular aggregate, into which a cell-containing solution is dispensed, a tip stocking portion 54, a tip imaging portion 55, a cell transfer portion 56 which receives a selected cellular aggregate, a black cover mounting portion 57, a tip disposal portion 58, and a preliminary treatment portion 59. Here, the cell selection portion 53 is a part in which a container corresponding to the first container 11 shown in FIGS. 5 and 6 is arranged, the cell transfer portion 56 is a part in which a container corresponding to the second container 12 is arranged, and the preliminary treatment portion 59 is a part in which a container corresponding to the third container 13 is arranged.

The head unit 61 includes a unit main body 611, a head portion 612, an X slider 613, and a Y slider 614. As shown in FIG. 12, the head portion 612 includes the above described plurality of heads 15, a first nozzle 615, and a second nozzle 616. In the present embodiment, an example is shown in which eight heads 15 are arranged in the X direction. The number of the heads 15 is arbitrary and may be arranged in matrix in an X-Y direction. The first nozzle 615 and the second nozzle 616 with a sucker 617 are installed into the unit main body 611 so as to be up and down movable and are internally provided with a piston mechanism which generates a sucking force and a discharging force. The unit main body 611 is internally provided with a head motor 171 (FIG. 14) corresponding to the second motor M2 shown in FIG. 6 and a tip motor 172 corresponding to the third motor, and a drive transmission mechanism therefor.

The X slider 613 is installed on the upper guide rail 433. On the upper guide rail 433, an X-axis motor 441 corresponding to the first motor M1 in FIG. 6 is provided. Operation of the X-axis motor 441 causes the X slider 613 to move in the X direction on the upper guide rail 433. The Y slider 614 supports the unit main body 611 at one end (a front end) in a Y direction. The Y slider 614 is installed on a Y rail (not shown in FIG. 11) arranged on an upper surface of the X slider 613. Operation of a Y-axis motor 442 (see FIG. 14) provided on the Y rail causes the Y slider 614 and the unit main body 611 to move in the Y direction. In other words, moving of the unit main body 611 along the upper guide rail 433 and the Y rail allows the head portion 612 to be freely movable in the X direction and the Y direction. Accordingly, the head portion 612 is allowed to move on the cell moving line 50 along a predetermined movement path above the base 42.

The illumination unit 62 is arranged to be movable above the base 42 in order to exclusively illuminate the cell selection portion 53 and the cell transfer portion 56 from above. The illumination is used as transmitted illumination when a cellular aggregate retained in the cell selection portion 53 or the cell transfer portion 56 is imaged by the imaging unit 63. The illumination unit 62 includes an illuminator 621 which emits an illumination light, an X slider 622, and a holder 623. The X slider 622 is installed to the middle guide rail 434. At the middle guide rail 434, an illumination unit driving motor 443 is provided. Operation of the driving motor 443 causes the X slider 622 to move on the middle guide rail 434 in the X direction. The holder 623 is installed so as to retain the illuminator 621, as well as to be movable with respect to the X slider 622 in the Y direction by a short distance by a driving device not shown. Accordingly, the illuminator 621 is movable above the base 42 in the X direction and the Y direction.

The imaging unit 63 is arranged to be movable below the base 42 in order to image cellular aggregates retained in the cell selection portion 53 and the cell transfer portion 56 from below the base 42. Further, in the present embodiment, the imaging unit 63 is used also in the tip imaging portion 55 for observing a state of attachment of the head 15 of the cylinder tip 1. The imaging unit 63 includes a camera 631, a vertical illuminator 632, an X slider 633, and a holder 634.

The camera 631 includes a CCD image sensor, and an optical system which forms an optical image on a light receiving surface of the CCD image sensor. The vertical illuminator 632 is a light source to be used when a target to be imaged by the camera 631 is not a light transmission body or is fluorescently stained, or other case. The X slider 633 is installed on the guide rail 413 of the supporting frame 41. At the guide rail 413, an imaging unit driving motor 444 is provided. Operation of the driving motor 444 causes the X slider 633 to move on the guide rail 413 in the X direction. The holder 634 is installed so as to retain the camera 631 and the vertical illuminator 632, as well as to be movable with respect to the X slider 633 in the Y direction by a short distance by a driving device not shown. Accordingly, the camera 631 is movable below the base 42 in the X direction and the Y direction.

Figure 13:
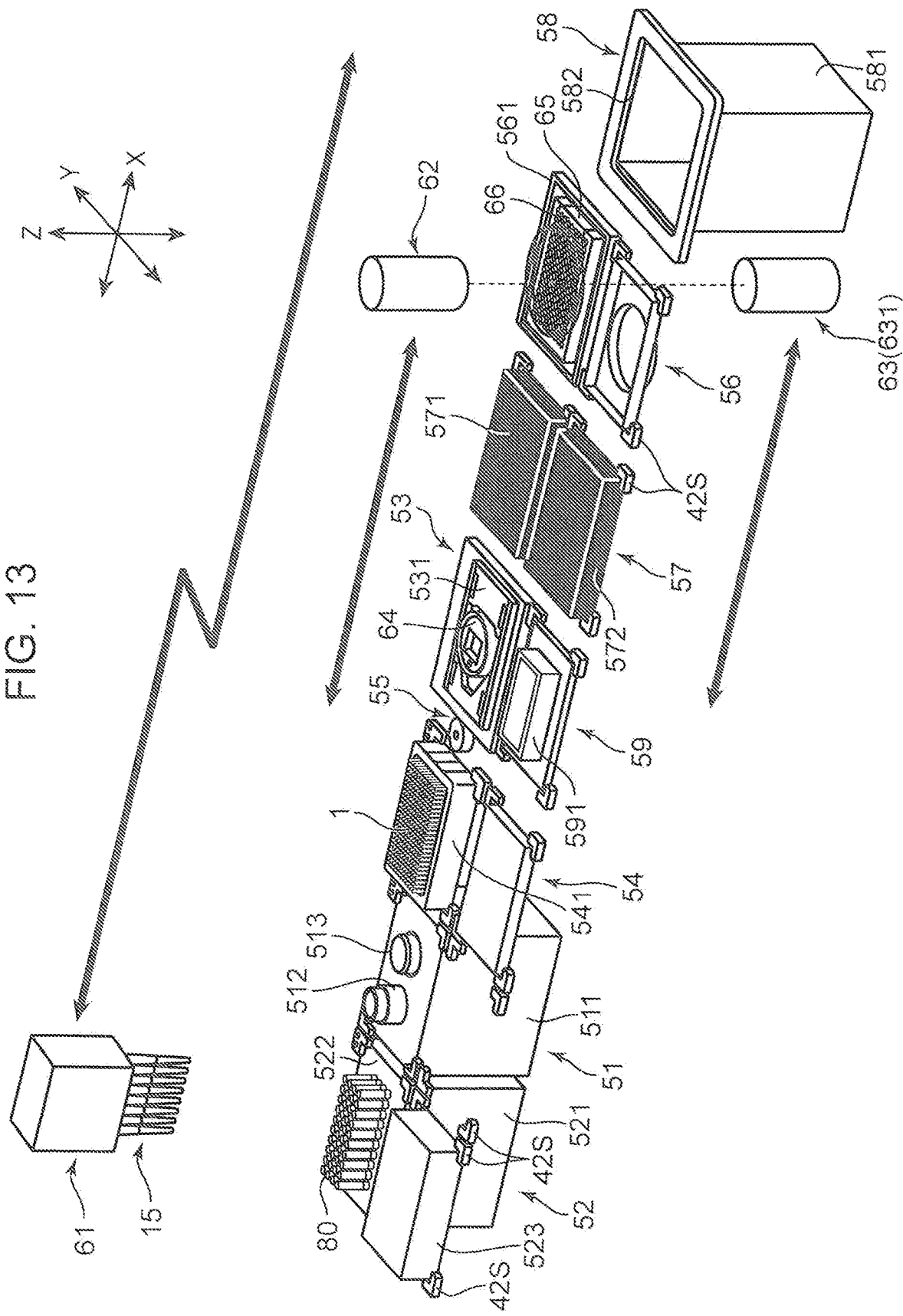
FIG. 13 is a perspective view showing constituent elements of a cell moving line in the cell moving device.

FIG. 13 is a perspective view showing the constituent elements picked up from the cell moving line 50 with illustration of the base 42 omitted. In FIG. 13, arrangement positions of the above head unit 61, illumination unit 62, and imaging unit 63 are also schematically shown. In the cell moving line 50, sequentially from an upstream side in the X direction (the left end side in FIG. 13), the dispensation tip stocking portion 52, the object stocking portion 51, the tip stocking portion 54, the tip imaging portion 55, the cell selection portion 53 and the preliminary treatment portion 59, the black cover mounting portion 57, and the cell transfer portion 56 and the tip disposal portion 58 are aligned. Each of these portions has a position thereof on the base 42 determined by a positioning member 42S.

The object stocking portion 51 is a part which stores a cell culture solution in which a large amount of cellular aggregates (objects) as a dispensation source are dispersed. The object stocking portion 51 includes a box 511 arranged at a predetermined position on the base 42, a tube 512 retained in the box 511, and a lid member 513 mounted on the box 511. The tube 512 is a cylindrical container with an upper surface opened and stores a cell culture solution containing cellular aggregates or impurities. The lid member 513 is a member for blocking the opening of the tube 512.

The dispensation tip stocking portion 52 is a part for keeping a plurality of dispensation tips 80. The dispensation tip 80 is an elongated tubular member which includes an upper end portion to be fit in the first nozzle 615, and a lower end portion including an opening provided at an edge thereof, the opening for sucking and discharging a cell culture solution. The dispensation tip 80 is attachable and detachable to/from the first nozzle 615. The dispensation tip 80 sucks a cell culture solution upon application of a sucking force by the first nozzle 615, as well as discharging the sucked cell culture solution upon application of the discharging force. The dispensation tip stocking portion 52 includes a retaining box 521 which retains the dispensation tips 80 arrayed in matrix in a vertically standing state, and a box lid member 523. Inside the retaining box 521, a holder member 522 is arranged for retaining the dispensation tips 80 in an aligned manner.

The cell selection portion 53 is a part for selecting a cellular aggregate of a desired size from the cell culture solution containing cellular aggregates or impurities of various sizes. The cell selection portion 53 includes a dish 64 and a retaining table 531. The dish 64 is a container with an upper surface opened, into which a cell culture solution containing cellular aggregates is dispensed by the dispensation tip 80 and in which the cell culture solution can be stored. The retaining table 531 retains the dish 64 so as to be positioned.

The dish 64, which is a container corresponding to the first container 11 as described before with reference to FIGS. 5 and 6, includes a well plate including, on a side of an upper surface thereof, a plurality of recessed portions for carrying cellular aggregates. With a through hole provided in a bottom portion of the recessed portion, cellular aggregates to be extracted are retained in the recessed portion and impurities and the like fall down from the through hole. Such selection of cellular aggregates and impurities results in leaving only the cellular aggregates on the well plate. The cellular aggregates being carried in the recessed portion are imaged by the camera 631 under lighting of the illumination unit 62. This enables specifying the positions of cellular aggregates which should be sucked.

The tip stocking portion 54 is a part which retains numbers of the above-described cylinder tips 1. The cylinder tip 1 is attachable and detachable to/from the head 15. The cylinder tip 1 serves a function of sucking cellular aggregates carried in the recessed portion of the above well plate, transporting the cellular aggregates along with movement of the head unit 61, and discharging the same to the cell transfer portion 56. The tip stocking portion 54 includes a retaining box 541 which retains numerous cylinder tips 1 arrayed in matrix in the vertically standing state. The cylinder tips 1 are retained in the retaining box 541 in a state where an upper end portions of the cylinder tips 1 are projected upward from an upper end surface of the retaining box 541. In other words, the cylinder tips 1 are retained in the retaining box 541 in a state of being easily attachable to the head 15 moving in a Z direction.

The tip imaging portion 55 is a pit which provides a position at which the cylinder tip 1 attached to the head 15 is imaged. The imaging is conducted by the imaging unit 63. At the time of imaging, the camera 631 of the imaging unit 63 is moved immediately under the tip imaging portion 55 to image each cylinder tip 1 under illumination of the vertical illuminator 632. Based on the image of the cylinder tip 1 and focal position information at the time of imaging, X, Y and Z coordinate positions of the front end opening 24 of the cylinder tip 1 are obtained. From a difference between the coordinate positions and a predetermined reference position, a correction value is derived. The correction value is used as a correction value at the time of controlling movement of the head 15.

The cell transfer portion 56 is a part arranged near an end portion on a downstream side of the cell moving line 50 in the X direction and serving as a movement destination of a cellular aggregate sucked from the dish 64 of the cell selection portion 53. The cell transfer portion 56 includes a microplate 65 and is a retaining table 561. The microplate 65 is a container corresponding to the second container 12 as described with reference to FIGS. 5 and 6, and is a plate on which numbers of small wells 66 with upper surfaces opened are arranged in matrix. The microplate 65 is formed of a translucent member, such as transparent plastic. In general, one cellular aggregate is housed in one well 66. Accordingly, a cellular aggregate being housed in each well 66 can be imaged by the camera 631. Additionally, an arrangement pitch of the well 66 is set to be substantially the same as an arrangement pitch of a group of the cylinder tips 1 attached to the aligned heads 15. This enables cellular aggregates to be simultaneously discharged from a group of the cylinder tips 1 to the well 66. The retaining table 561 retains the microplate 65 so as to be positioned.

The black cover mounting portion 57 is a part on which a first black cover 571 to be put on the cell transfer portion 56 and a second black cover 572 to be put on the cell selection portion 53 are mounted. The first and second black covers 571 and 572 are light shielding bodies for use when in a shaded state, cellular aggregate carried by the dish 64 or the microplate 65 are imaged. For example, when a fluorescent agent is added to a cell culture solution to conduct fluorescent observation of cellular aggregates, the first and second black covers 571 and 572 are put on the retaining tables 531 and 561 so as to cover the same.

The tip disposal portion 58 is a part which is arranged at an end portion on the most downstream side of the cell moving line 50 in the X direction and in which the cylinder tip 1 and the dispensation tip 80 having been used after the above sucking and discharging operation are disposed of. The tip disposal portion 58 includes a collection box 581 for housing the cylinder tip 1 and the dispensation tip 80 having been used. At the time of the disposal, the head unit 61 equipped with the cylinder tip 1 or the dispensation tip 80 is moved onto an opening portion 582 of the collection box 581 to execute operation of detaching the cylinder tip 1 or the dispensation tip 80 from the head portion 612. The detaching operation causes the cylinder tip 1 or the dispensation tip 80 to fall down into the collection box 581 through the opening portion 582.

The preliminary treatment portion 59 is a part which is arranged adjacent to the cell selection portion 53 in the Y direction and on which a reservoir 591 storing a preliminary treatment solution is mounted. The reservoir 591 is a container corresponding to the third container 13 as described with reference to FIGS. 5 and 6, and the preliminary treatment solution is a liquid to be sucked into the cylinder tip 1 before first use after attachment to the head 15 as described before. Here, as the preliminary treatment solution, a cell culture solution is used. The reservoir 591 may be arranged adjacent to the tip stocking portion 54 in the Y direction, or may be arranged in a space provided between the tip imaging portion 55 and the cell selection portion 53.

Figure 14:
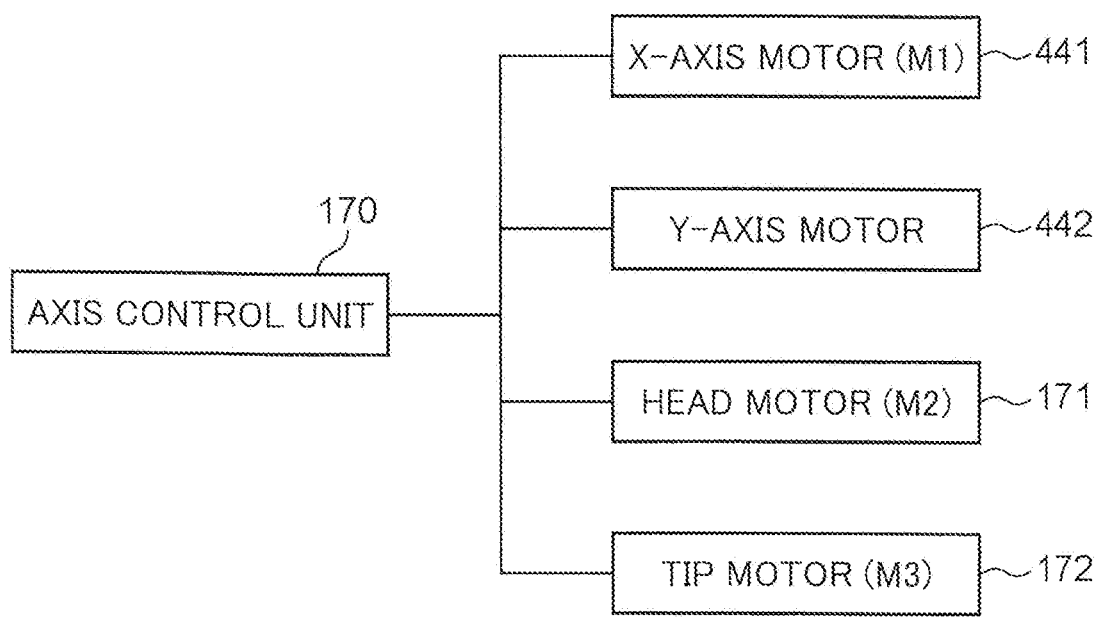
FIG. 14 is a block diagram showing a control configuration of a head device.

FIG. 14 is a block diagram showing a control configuration of the head unit 61. The cell moving device 4 includes an axis control unit 170 (a control unit) for controlling movement of the head 15 and the plunger rod 153 therein (FIG. 1) in the up-down direction and controlling movement of the head unit 61 in the X direction, the Y direction, and the Z direction. The axis control unit 170 controls drive of the above X-axis motor 441 and Y-axis motor 442 (the head moving mechanism), the head motor 171, and the tip motor 172.

The axis control unit 170 controls movement of the head unit 61 in the X direction and the Y direction by controlling the X-axis motor 441 corresponding to the first motor M1 in FIG. 6 and the Y-axis motor 442. Specifically, the axis control unit 170 drives the X-axis motor 441 and the Y-axis motor 442 such that the head unit 61 moves on the cell moving line 50 along a predetermined movement path.

The head motor 171 is a motor corresponding to the second motor M2 in FIG. 6 and the tip motor 172 is a motor corresponding to the third motor M3. By controlling drive of the head motor 171, the axis control unit 170 controls a position in height of the head 15 in the Z direction. Additionally, by controlling drive of the tip motor 172, the axis control unit 170 causes the plunger rod 153 to move up and down, thereby controlling suction of a preliminary treatment solution into the cylinder tip 1, the cellular aggregate sucking and discharging operation, and the like. Other than these operations, the axis control unit 170 also controls operation of causing the first nozzle 615 and the second nozzle 616 with the sucker 617 (FIG. 12) to move up and down and operation of the piston mechanism to generate a sucking force and a discharging force at these nozzles 615 and 616.

Figure 15:
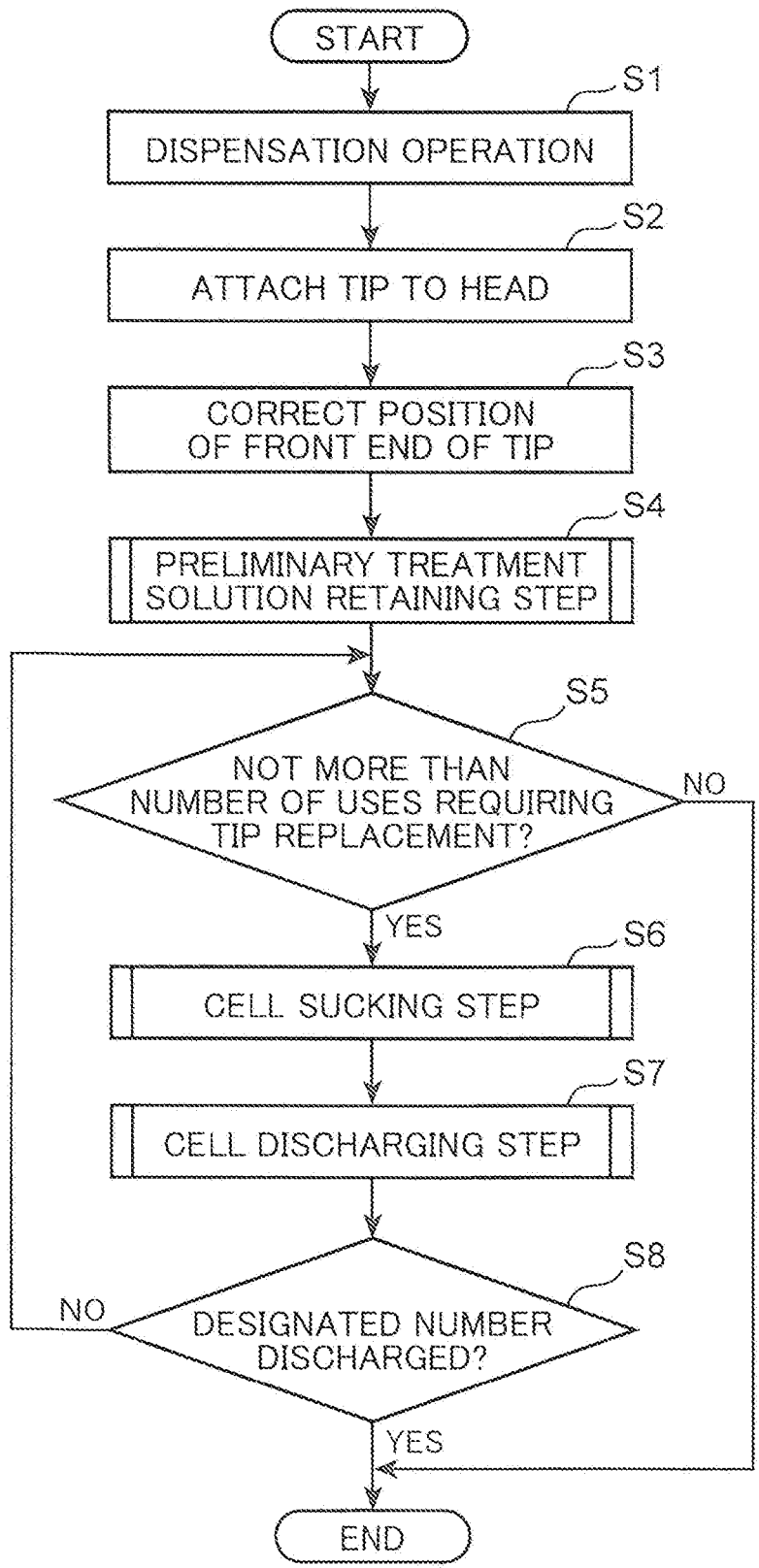
FIG. 15 is a flow chart showing operation of the cell moving device.

Subsequently, operation of the cell moving device 4 will be described based on FIGS. 11 to 14, and the flow charts shown in 15 to 18. FIG. 15 is the flow chart of the entire step to be executed by the cell moving device 4. The axis control unit 170 first causes dispensation operation to be executed (Step S1). The dispensation operation is operation of sucking a cell culture solution stocked in the tube 512 by a predetermined amount and discharging the same to the dish 64, the cell culture solution in which a large amount of the cellular aggregate C is dispensed.

For this dispensation operation, the axis control unit 170 causes the following control A1 to A4 to be sequentially executed. More specifically, the control includes (A1) of moving the head unit 61 onto the dispensation tip stocking portion 52 to attach the dispensation tip 80 to the first nozzle 615, (A2) of moving the head unit 61 onto the object stocking portion 51 to suck, into the dispensation tip 80, a predetermined dispensation amount of a cell culture solution containing cellular aggregates stored in the tube 512, (A3) of moving the head unit 61 onto the cell selection portion 53 to discharge the cell culture solution in the dispensation tip 80 to the dish 64, and (A4) of moving the head unit 61 onto the tip disposal portion 58 to detach the dispensation tip 80 having been used from the first nozzle 615 and dispose of the same into the collection box 581.

Subsequently, cell moving operation using the cylinder tip 1 is executed. The axis control unit 170 conducts control of attaching the cylinder tip 1 to the head 15 (Step S2). To be specific, the axis control unit 170 drives the X-axis motor 441 and as required, the Y-axis motor 442 to move the head unit 61 onto the tip stocking portion 54. On this occasion, for one cylinder tip 1, one head 15 is positioned. Then, the axis control unit 170 drives the head motor 171 to cause the positioned head 15 to fall down such that to the front end of the head 15, the cylinder tip 1 is attached.

After the attachment, the head unit 61 is moved to the tip imaging portion 55 to image the cylinder tip 1 attached to the head 15. The imaging enables sensing of a state of the cylinder tip 1 being attached to the head 15 to obtain X, Y and Z coordinates of the front end opening 24 of the cylinder tip 1. This leads to recognition of a positional displacement of the front end opening 24 from a position of a front end of the head 15 to obtain correction values of the X, Y and Z coordinates for moving the head 15 (Step S3).

Thereafter, the axis control unit 170 executes the preliminary treatment solution retaining step (the first control) as described above based on FIGS. 7A to 7C (Step S4). The axis control unit 170 causes the head unit 61 to move to the preliminary treatment portion 59 so as to suck the preliminary treatment solution stored in the reservoir 591 into the cylinder tip 1.

Next, determination is made whether the number of uses of the cylinder tip 1 attached to the head 15 is not more than a predetermined number of uses requiring replacement (Step S5). The cylinder tip 1 commonly needs replacement when a cellular aggregate sucking and discharging operation cycle is executed on the order of one to 50 times. This is because execution of the cycle causes cell fragments or impurities to remain in the cylinder tip 1 to hinder movement of a target cellular aggregate.

When the number of uses of the cylinder tip 1 is not more than the predetermined number of uses requiring replacement (YES in Step S5), the axis control unit 170 executes the cell sucking step (the second control) as described before based on FIGS. 8A to 8D and FIGS. 9A to 9C (Step S6). Subsequently, the axis control unit 170 executes the cell discharging step (the third control) as described before based on FIGS. 10A to 10C (Step S7).

Thereafter, it is checked whether a designated number of cellular aggregates set in advance have been discharged or not (Step S8). The designated number is, for example, the number of the wells 66 provided in the microplate 65. In this case, upon confirming that cellular aggregates have been moved to all the wells 66, determination is made that discharge of the designated number of cellular aggregates is ended (YES in Step S8) to end the processing. Also, when the number of uses of the cylinder tip 1 reaches the number of uses requiring replacement (NO in Step S5), the processing is ended. On the other hand, when determination is made that discharging of the designated number of cellular aggregates has not been completed (NO in Step S8), the procedure returns to Step S5 to repeat the processing. In other words, since the cylinder tip 1 already has the preliminary treatment solution and the tubular passage 2P is wet, the preliminary treatment solution retaining step does not be executed any more.

Figure 16:
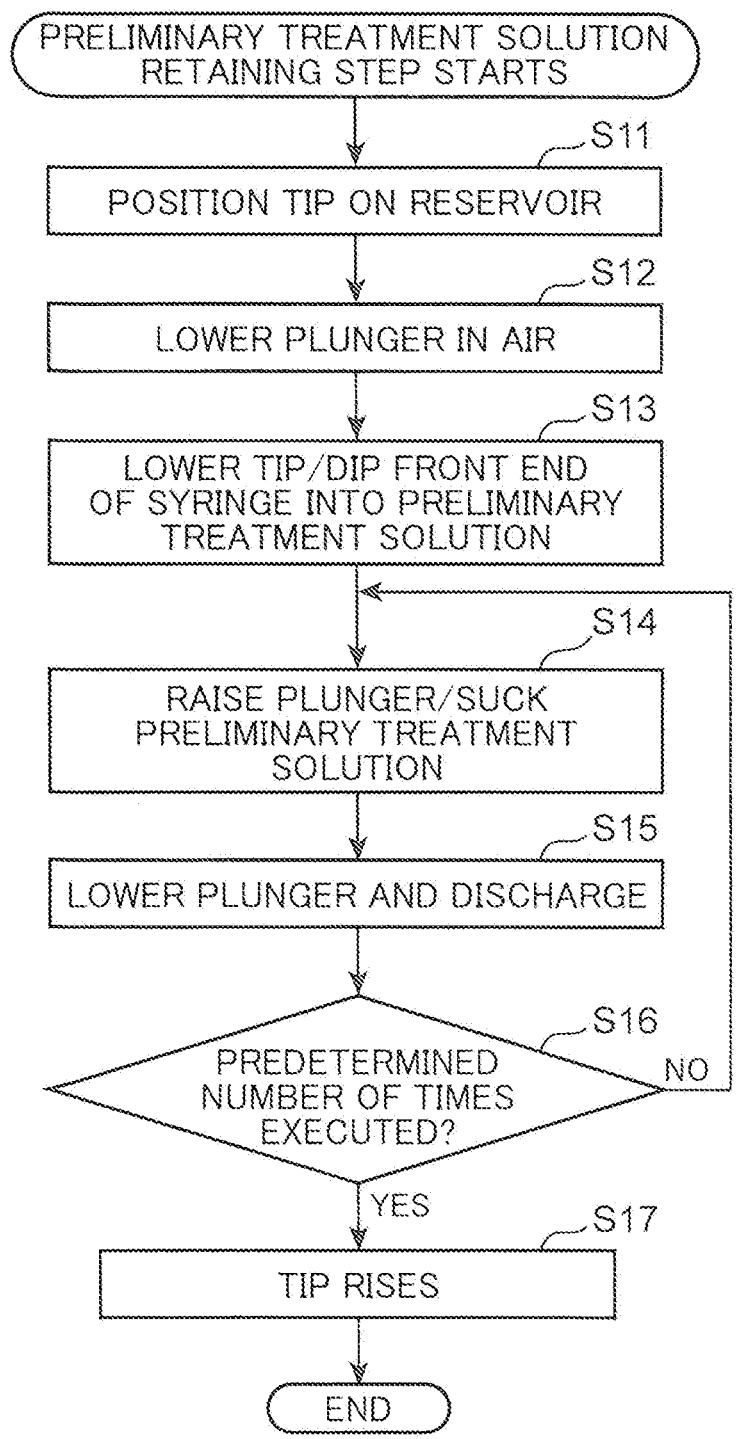
FIG. 16 is a flow chart showing operation of the cell moving device.

FIG. 16 is a flow chart showing details of the preliminary treatment solution retaining step in FIG. 15 (Step S4). The axis control unit 170 drives the X-axis motor 441 and the Y-axis motor 442 to move the head unit 61 onto the preliminary treatment portion 59. The head 15 to which the cylinder tip 1 is attached is positioned so as face to the preliminary treatment solution stored in the reservoir 591 (Step S11). Additionally, in order to attain the state shown in FIG. 7A where the plunger 3 is inserted deepest into the syringe 2, the axis control unit 170 drives the tip motor 172 to cause the plunger rod 153 to fall down (Step S12).

Subsequently, the axis control unit 170 drives the head motor 171 to cause the head 15 (the cylinder tip 1) to fall down until the front end portion 2T of the syringe 2 dips into the preliminary treatment solution in the reservoir 591 (Step S13). Then, the axis control unit 170 drives the tip motor 172 to cause the plunger 3 to rise by a predetermined distance (Step S14). This results in sucking the preliminary treatment solution into the tubular passage 2P from the front end opening 24 of the syringe 2. The axis control unit 170 subsequently causes this time the plunger 3 to fall down by a predetermined distance (Step S15). As a result, a part of the preliminary treatment solution sucked into the tubular passage 2P is discharged to the reservoir 591. This operation is as described with reference to FIG. 7C.

Thereafter, the axis control unit 170 checks whether the cycle composed of the sucking at Step S14 and the discharging at Step S15 has been executed a predetermined number of times (Step S16). When the number of executions is yet to reach the predetermined number of times (NO in Step S16), the procedure returns to Step S14 to repeat the processing. On the other hand, when reaching the predetermined number of times (YES in Step S16), the axis control unit 170 drives the head motor 171 to cause the cylinder tip 1 to rise (Step S17) and ends the processing.

Figure 17:
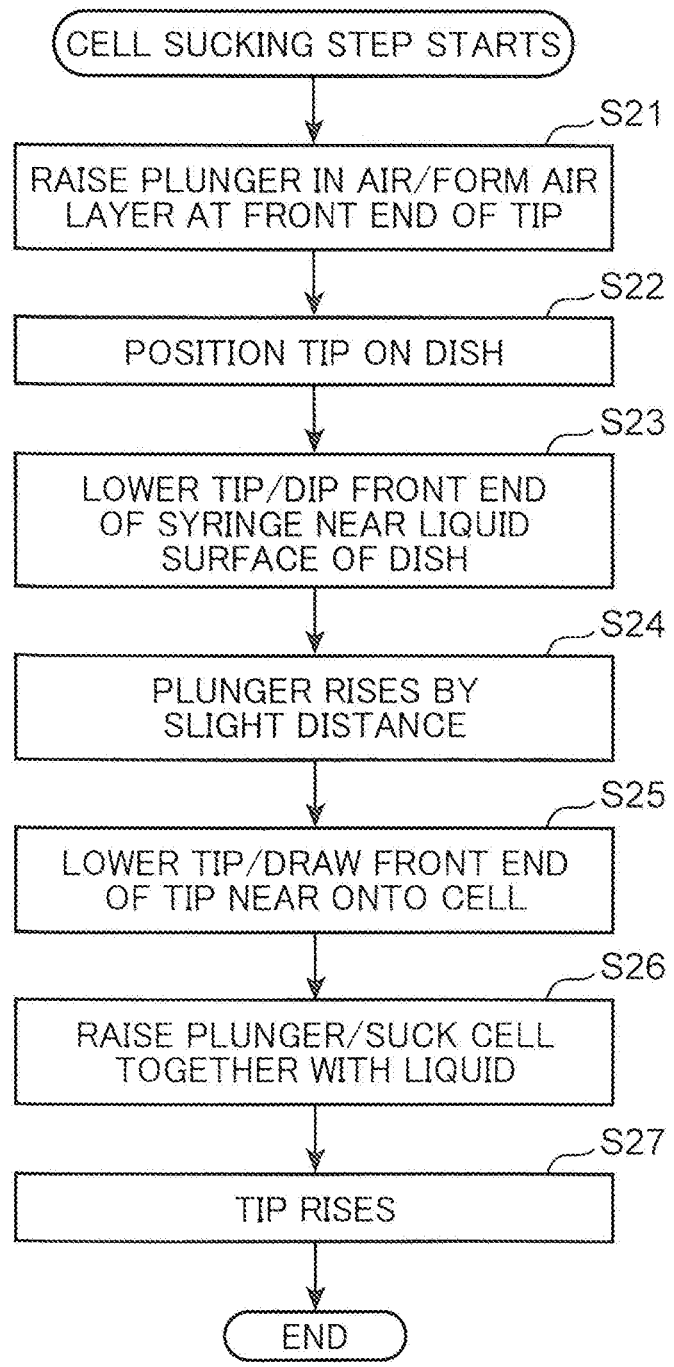
FIG. 17 is a flow chart showing operation of the cell moving device.

FIG. 17 is a flow chart showing details of the cell sucking step (Step S6). First, the axis control unit 170 executes the step (the fourth control) of forming an air layer in the tubular passage 2P as shown before in FIGS. 8A and 8B (Step S21). To be specific, in a state where the cylinder tip 1 is present in the air, the axis control unit 170 drives the tip motor 172 to cause the plunger 3 to rise by a predetermined length. As a result, the air layer H is formed in the tubular passage 2P near the front end opening 24 of the syringe 2.

Subsequently, the axis control unit 170 drives the Y-axis motor 442 to cause the head unit 61 to move above the dish 64 of the cell selection portion 53. At this time, one of the heads 15 to which the cylinder tip 1 is attached is positioned so as to be arranged on a vertical line of one cellular aggregate in the dish 64 (Step S22). On this occasion, the correction data obtained before in Step S3 is used as positioning data of the head 15.

Thereafter, the axis control unit 170 executes such pre-treatment step as shown before in FIGS. 9A to 9C. Specifically, the axis control unit 170 drives the head motor 171 to cause the head 15 to fall down until the front end portion 2T of the syringe 2 is dipped in a vicinity of a surface of the cell culture solution in the dish 64 (Step S23). Then, the axis control unit 170 drives the tip motor 172 to cause the plunger 3 to rise by a slight distance (Step S24). As a result, a small amount of the cell culture solution is sucked into the tubular passage 2P near the front end opening 24.

Next, the axis control unit 170 executes such cellular aggregate sucking step as shown before in FIGS. 8C and 8D. The axis control unit 170 drives the head motor 171 to cause the cylinder tip 1 to fall down so as to dip the front end opening 24 into the cell culture solution in the dish 64, as well as drawing the front end opening 24 near to a cellular aggregate as a sucking target (Step S25). Then, the axis control unit 170 drives the tip motor 172 to cause the plunger 3 to rise by a predetermined distance, thereby sucking the cellular aggregate into the tubular passage 2P from the front end opening 24 (Step S26). Thereafter, the axis control unit 170 drives the head motor 171 to cause the cylinder tip 1 to rise (Step S27), and ends the processing.

Figure 18:
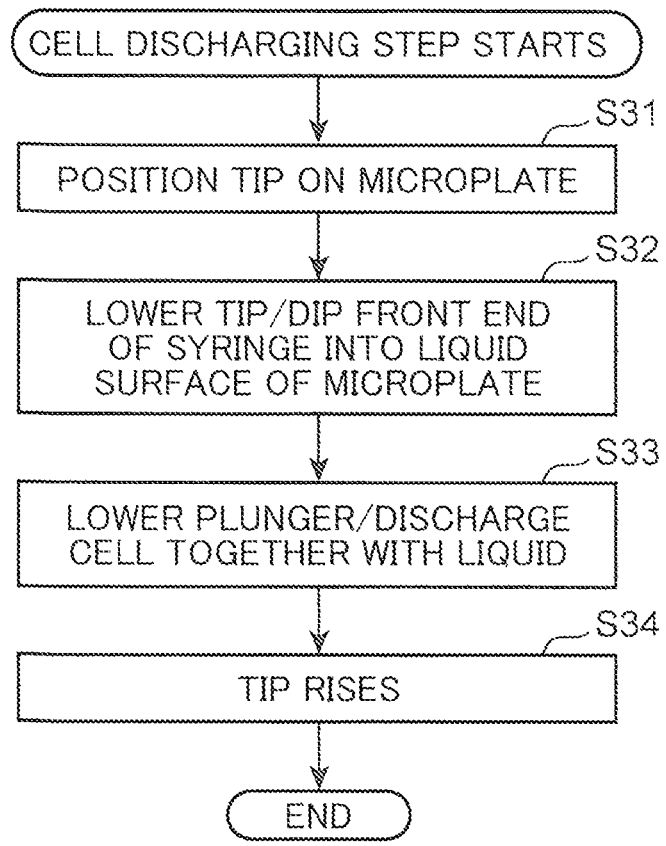
FIG. 18 is a flow chart showing operation of the cell moving device.

FIG. 18 is a flow chart showing details of the cell discharging step (Step S7). The axis control unit 170 drives the X-axis motor 441 to cause the head unit 61 to move above the microplate 65 of the cell transfer portion 56. At this time, one of the heads 15 to which the cylinder tip 1 is attached is positioned so as to be arranged on a vertical line of one of the wells 66 in the microplate 65 (Step S31).

Next, the axis control unit 170 executes such cellular aggregate discharging step as shown before in FIGS. 10B and 10C. The axis control unit 170 drives the head motor 171 to cause the cylinder tip 1 to fall down so as to dip the front end opening 24 into the cell culture solution in the microplate 65, as well as drawing the front end opening 24 near to one well 66 as a target (Step S32). Then, the axis control unit 170 drives the tip motor 172 to cause the plunger 3 to fall down by a predetermined distance, thereby discharging the sucked cellular aggregate from the front end opening 24 to the well 66 together with the cell culture solution (Step S33). Thereafter, the axis control unit 170 drives the head motor 171 to cause the cylinder tip 1 to rise (Step S34) and ends the processing.

Although the above cell moving device 4 has been described with respect to an example where the reservoir 591 which stores a preliminary treatment solution is provided, the function of the reservoir 591 as a container may be served by another container. For example, a cell culture solution is stored in the dish 64 provided in the cell selection portion 53. The cell culture solution may be used as a preliminary treatment solution. In this case, it is preferable to provide, in the dish 64, a region where the cylinder tip 1 enters in the preliminary treatment solution retaining step (a region into which the cellular aggregate C is not sucked).

Other than the above, the function of the reservoir 591 may be served by the microplate 65 of the cell transfer portion 56. Also in this case, it is preferable to provide, in the microplate 65, a dedicated port through which the cylinder tip 1 enters in the preliminary treatment solution retaining step. Further, liquid to be a preliminary treatment solution may be stored in the retaining box 541 of the tip stocking portion 54 which stocks the cylinder tip 1 yet to be used.

The above-described specific embodiment mainly includes the disclosure having the following configurations.

An object moving method according to one aspect of the present disclosure includes a step of preparing a tip including a syringe having a front end opening for sucking an object and a tubular passage with one end leading to the front end opening, and a plunger which reciprocates in the tubular passage; a step of dipping the front end opening of the syringe into a predetermined preliminary treatment solution and causing the plunger to reciprocate, thereby retaining the preliminary treatment solution in a space between the tubular passage and the plunger; a step of dipping the front end opening of the syringe into a liquid containing an object and causing the plunger to rise, thereby sucking the object into the tubular passage together with the liquid; and a step of causing the plunger to fall down to discharge the object outside together with the liquid.

This method includes a step of retaining the preliminary treatment solution in a space between the tubular passage of the syringe and the plunger before sucking and discharging an object by the tip. This results in filling the space with the preliminary treatment solution in advance, so that an object introduced into the tip in the subsequent sucking step is not easily allowed to enter the space. Accordingly, the object sucked into the tip is suppressed from being caught between the syringe and the plunger to allow the object to have excellent discharging property.

The above object moving method preferably includes, between the step of retaining the preliminary treatment solution and the sucking step, a step of arranging the front end opening of the syringe in the air and causing the plunger to rise by a predetermined length to form an air layer in the tubular passage near the front end opening.

According to this method, the air layer functions as a seal layer which separates, in the tubular passage, the preliminary treatment solution retained in advance in the tip and a liquid containing the object sucked thereafter. Accordingly, it is possible to eliminate a possibility that the sucked object moves into the preliminary treatment solution. Additionally, this prevents the preliminary treatment solution from being mixed with the liquid, or prevents the preliminary treatment solution from being discharged to the second container at the discharging step.

In the above case of forming the air layer, the sucking step preferably includes a step of retaining a small amount of the liquid near the front end opening by causing the plunger to rise by a slight distance after dipping the front end opening of the syringe into the liquid containing the object; and a step of sucking the object from the front end opening into the tubular passage by causing the plunger to rise by a predetermined distance after arranging the front end opening near above the object.

This method eliminates even air accumulated near the front end opening by the rise of the plunger by a slight distance. Then, because this brings a state where a small amount of the liquid is retained near the front end opening, the object can be subsequently sucked smoothly.

In the above object moving method, it is preferable that the object is a cell and the liquid is a medium. This method allows the present disclosure to be applicable to medical or biological studies.

An object moving device according to another aspect of the present disclosure includes a first container which stores a liquid containing an object; a second container which receives the object; a third container which stores a preliminary treatment solution; a tip including a syringe having a front end opening for sucking the object and a tubular passage with one end leading to the front end opening, and a plunger which reciprocates in the tubular passage; a head to which the tip is attached and includes a rod that reciprocates the plunger; a head moving mechanism which causes the head to move among the first container, the second container, and the third container; and a control unit which controls operation of the head and the head moving mechanism, in which the control unit executes first control of causing the head to move to a position of the third container to dip the front end opening of the syringe into a preliminary treatment solution in the third container and cause the plunger to reciprocate, thereby retaining the preliminary treatment solution in a space between the tubular passage and the plunger; second control of causing the head to move to a position of the first container to dip the front end opening of the syringe into the liquid in the first container and cause the plunger to rise, thereby sucking the object into the tubular passage together with the liquid, and third control of causing the head to move to a position of the second container to cause the plunger to fall down, thereby discharging the object to the second container together with the liquid.

In this device, before sucking and discharging an object by the tip, the control unit causes the first control to be executed of retaining a preliminary treatment solution in a space between the tubular passage of the syringe and the plunger. This allows the space to be filled with the preliminary treatment solution in advance, thereby preventing the object introduced into the tip by the subsequent second control from easily entering the space. Accordingly, the object sucked in the tip is suppressed from being caught between the syringe and the plunger, so that the object is allowed to have excellent discharging property at the execution of the third control.

In the object moving device, between the first control and the second control, the control unit preferably executes fourth control of arranging the front end opening of the syringe in the air and causing the plunger to rise by a predetermined length to form an air layer in the tubular passage near the front end opening.

In this device, the air layer functions as a seal layer which separates, in the tubular passage, the preliminary treatment solution retained in advance in the tip by the execution of the first control and a liquid containing the object to be sucked by the subsequent second control. Accordingly, it is possible to eliminate a possibility that the sucked object moves into the preliminary treatment solution. Additionally, this prevents the preliminary treatment solution from being mixed with the liquid, or prevents the preliminary treatment solution from being discharged to the third container at the execution of the third control.

In the above object moving device, the liquid stored in the first container or in the second container and the preliminary treatment solution stored in the third container are preferably substantially equal in component to each other.

In the above method, since the preliminary treatment solution is sucked in advance, even when the air layer is provided, an inner wall of the tubular passage can be wetted with the preliminary treatment solution. However, making a liquid containing an object and a preliminary treatment solution be substantially equal in component to each other prevents even mixture of both the liquids from causing any influence.

In the above object moving device, it is preferable that the object is a cellular aggregate, the liquid is a cell culture solution, the first container is a dish for selecting a cellular aggregate of a predetermined size, the second container is a microplate including a well which houses the cellular aggregate, and the third container is a reservoir which stores the cell culture solution.

This device allows the present disclosure to be applicable to a cell moving device which selects and moves a cellular aggregate.

As described in the foregoing, the present disclosure provides a method and a device for moving an object which enable an object once sucked into a tip to be discharged satisfactorily without being trapped in the tip.

The invention claimed is:

1. An object moving method comprising:
preparing a tip including a syringe having a front end opening for sucking an object and a tubular passage with one end leading to the front end opening, and a plunger which reciprocates in the tubular passage;
dipping the front end opening of the syringe into a predetermined preliminary treatment solution and causing the plunger to reciprocate, thereby retaining the preliminary treatment solution in a space between the tubular passage and the plunger,
while retaining the preliminary treatment solution in a space between the tubular passage and the plunger, dipping the front end opening of the syringe into a liquid containing the object and causing the plunger to rise, thereby sucking the object into the tubular passage together with the liquid; and causing the plunger to fall down to discharge the object outside together with the liquid.

2. The object moving method according to claim 1, comprising:

between retaining the preliminary treatment solution and sucking, arranging the front end opening of the syringe in air and causing the plunger to rise by a predetermined length to form an air layer in the tubular passage near the front end opening.

3. The object moving method according to claim 2, wherein the sucking comprises:

retaining a small amount of the liquid near the front end opening by causing the plunger to rise by a slight distance after dipping the front end opening of the syringe into the liquid containing the object; and sucking the object from the front end opening into the tubular passage by causing the plunger to rise by a predetermined distance after arranging the front end opening near above the object.

4. The object moving method according to claim 3, wherein the object is a cell and the liquid is a medium.

5. The object moving method according to claim 2, wherein the object is a cell and the liquid is a medium.

6. The object moving method according to claim 1, wherein the object is a cell and the liquid is a medium.

* * * * *